United States Patent [19]
Lambert et al.

[11] Patent Number: 6,028,246
[45] Date of Patent: Feb. 22, 2000

[54] *BACILLUS THURINGIENSIS* STRAINS AND THEIR INSECTICIDAL PROTEINS

[75] Inventors: Bart Lambert, Beernem; Stefan Jansens, Ghent; Katrien Van Audenhove, Ghent; Marnix Peferoen, Ghent, all of Belgium

[73] Assignee: Plant Genetic Systems, N.V., Brussels, Belgium

[21] Appl. No.: 08/455,838

[22] Filed: May 31, 1995

Related U.S. Application Data

[62] Division of application No. 08/379,656, Mar. 23, 1995.

[30] Foreign Application Priority Data

Aug. 27, 1992 [EP] European Pat. Off. .............. 92402358
Apr. 9, 1993 [EP] European Pat. Off. .............. 93400949
Jul. 12, 1993 [WO] WIPO ...................... PCT/EP93/01820

[51] Int. Cl.$^7$ .......................... C12N 15/32; C12N 15/82; A01H 4/00; A01H 5/00
[52] U.S. Cl. ................... 800/205; 800/DIG. 55; 800/DIG. 56; 435/69.1; 435/172.3; 435/320.1; 435/419; 536/23.71
[58] Field of Search ..................... 800/205, 250, 800/DIG. 56, DIG. 55; 435/69.1, 240.4, 172.3; 536/23.7, 23.71; 47/58

[56] References Cited

FOREIGN PATENT DOCUMENTS

| | | |
|---|---|---|
| 0358557 | 8/1990 | European Pat. Off. . |
| 0498537 | 4/1992 | European Pat. Off. . |
| 9006999 | 2/1990 | WIPO . |
| 9304587 | 3/1991 | WIPO . |

OTHER PUBLICATIONS

Smulevitch et al., FEBS Letters, 298, 25–28 (1991).
Vaeck et al., Nature, 328, 33–37 (1987).
Hofte et al., Microbiological Reviews, 53, 242–255 (1989).
Gleave et al. Journal of General Microbiology 138: 55–62 1992 Identification of an Insecticidal Crystal Protein from Bacillus . . . .
Perlak et al. Bio/Technology vol. 8: 939–943 Oct. 1990 Insect Resistant Cotton Plants.
Perlak et al. Proc. Natl. Acad. Sci. USA vol. 88: 3324–3328 Apr. 1991 Modification of The Coding Sequence Enhances Plant Expression . . . .

*Primary Examiner*—Douglas W. Robinson
*Assistant Examiner*—Thomas Haas
*Attorney, Agent, or Firm*—Birch, Stewart, Kolasch & Birch, LLP

[57] ABSTRACT

Four novel Bacillus thuringiensis strains, which are deposited at the BCCM-LMG under accession nos. LMG P-12592, LMG P-12593, LMG P-12594, and LMG P-13493, produce new crystal proteins during sporulation that are toxic to Lepidoptera, more particularly against Noctuidae such as spodoptera spp. and Agotis ipsilon, against Pyralidae such as Ostrinia nubilalis, and against Yponomeutidae such as Plutella xylostella, and that are encoded by a novel gene. The crystal proteins contain protoxins, which can yield a toxin as trypsin-digestion product. A plant, the genome of which is transformed with a DNA sequence that comes from either one of the strains nd that encodes its respective toxin, is resistant to Lipidoptera. Each strain, itself, or its crystal, crystal protein, protoxin or toxin can be used as the active ingredient in an insecticidal composition for combating Lepidoptera.

17 Claims, 1 Drawing Sheet

BACILLUS THURINGIENSIS STRAINS AND THEIR INSECTICIDAL PROTEINS

This application is a divisional of copending application Ser. No. 08/379.656, filed on Mar. 23, 1995, the entire contents of which are hereby incorporated by reference.

This invention relates to four novel strains of *Bacillus thuringiensis* (the "BTS02617A strain", the "BTS02618A strain", the "BTS02654B strain" and the "BTS02652E strain"), each of which produces crystallized proteins (the "BTS02617A crystal proteins", the "BTS02618A crystal proteins", the "BTS02654B crystal proteins" and the "BTS02652E crystal proteins", respectively) which are packaged in crystals (the "BTS02617A crystals", the "BTS02618A crystals", the "BTS02654B crystals" and the "BTS02652E crystals", respectively) during sporulation. The BTS02617A, BTS02618A, BTS02654B and BTS02652E strains were deposited under the provisions of the Budapest Treaty at the Belgian Coordinated Collections of Microorganisms—Collection Laboratorium voor Microbiologie Belgium ("BCCM-LMG"), R.U.G., K. Ledeganckstraat 35, B-9000 Gent.

This invention also relates to an insecticide composition that is active against Lepidoptera and that comprises the BTS02617A, BTS02618A, BTS02654B or BTS02652E strain, as such, or preferably the BTS02617A, BTS02618A, BTS02654B or BTS02652E crystals, crystal proteins or the active component(s) thereof as an active ingredient.

This invention further relates to a gene (the "bTS02618A gene"), which is present in the genome of the BTS02617A, BTS02618A, BTS02654B and BTS02652E strains and which encodes an insecticidal protein (the "BTS02618A protoxin") that is found in the BTS02617A, BTS02618A, BTS02654B and BTS02652E crystals. The BTS02618A protoxin is the protein that is produced by the BTS02617A, BTS02618A, BTS02654B and BTS02652E strains before being packaged into their respective BTS02617A, BTS02618A, BTS02654B and BTS02652E crystals.

This invention still further relates to a toxin (the "BTS02618A toxin") which can be obtained (e.g., by trypsin digestion) from the BTS02618A protoxin. The BTS02618A toxin is an insecticidally active protein which can be liberated from the BTS02617A crystals, the BTS02618A crystals, the BTS02654B crystals, and the BTS02652E crystals, which are produced by the BTS02617A strain, the BTS02618A strain, the BTS02654B strain and the BTS02652E strain, respectively. This toxin and its protoxin have a high activity against a wide range of lepidopteran insects, particularly against Noctuidae, especially against Spodoptera and Agrotis spp., but also against other important lepidopteran insects such as Pyralidae, particularly the European corn borer, *Ostrinia nubilalis*, and Yponomeutidae such as *Plutella xylostella*. This new characteristic of the BTS02618A protoxin and toxin ("(pro)toxin"), i.e., the combination of activity against different economically important Lepidopteran insect families such as Noctuidae, Yponomeutidae and Pyralidae, makes this (pro)toxin an ideally suited compound for combatting a wide range of insect pests by contacting these insects with the (pro)toxin, e.g., by spraying or by expressing the bTS02618A gene in plant-associated bacteria or in plants. The BTS02618A toxin is believed to represent the smallest portion of the BTS02618A protoxin which is insecticidally effective against Lepidoptera.

This invention yet further relates to a chimeric gene that can be used to transform a plant cell and that contains the following operably linked DNA fragments:

1) a part of the bTS02618A gene (the "insecticidally effective bTS02618A gene part") encoding an insecticidally effective portion of the BTS02618A protoxin, preferably a truncated part of the bTS02618A gene (the "truncated bTS02618A gene") encoding just the BTS02618A toxin;

2) a promoter suitable for transcription of the insecticidally effective bTS02618A gene part in a plant cell; and 3) suitable 3' end transcript formation and polyadenylation signals for expressing the insecticidally effective bTS02618A gene part in a plant cell.

This chimeric gene is hereinafter generally referred to as the "bTS02618A chimeric gene".

This invention also relates to:

1) a cell (the "transformed plant cell") of a plant, such as corn or cotton, the genome of which is transformed with the insecticidally effective bTS02618A gene part, preferably the bTS02618A chimeric gene; and 2) a plant (the "transformed plant") which is regenerated from the transformed plant cell or is produced from the so-regenerated plant and their seeds, the genome of which contains the insecticidally effective bTS02618A gene part, preferably the bTS02618A chimeric gene, and which is resistant to Lepidoptera.

This invention still further relates to:

1) a microbial organism, such as *B. thuringiensis* or Pseudomonas spp., the genome of which is transformed with all or part of the bTS02618A gene; and 2) a microbial spore, containing a genome which is transformed with all or parts of the bTS02618A gene.

BACKGROUND OF THE INVENTION

*B. thurinciensis* ("*Bt*") is a Gram-positive bacterium which produces endogenous crystals upon sporulation. The crystals are composed of proteins which are specifically toxic against insect larvae. These crystal proteins and corresponding genes have been classified based on their structure and insecticidal spectrum (Höfte and Whiteley, 1989). The four major classes are Lepidoptera-specific (cryI), Lepidoptera- and Diptera-specific (cryII), Coleoptera-specific (cryII), and Diptera-specific (cryIV) genes.

The fact that conventional submerged fermentation techniques can be used to produce *Bt* spores on a large scale makes *Bt* bacteria commercially attractive as a source of insecticidal compositions.

Gene fragments from some *Bt* strains, encoding insecticidal proteins, have heretofore been identified and integrated into plant genomes in order to render the plants insect-resistant. However, obtaining expression of such *Bt* gene fragments in plants is not a straightforward process. In order to achieve optimal expression of an insecticidal protein in plant cells, it has been found necessary to engineer each *Bt* gene fragment in a specific way so that it encodes a part of a *Bt* protoxin that retains substantial toxicity against its target insects (European patent application ("EPA") 86/300, 291.1 and 88/402,115.5; U.S. patent application Ser. No. 821,582, filed Jan. 22, 1986).

SUMMARY OF THE INVENTION

In accordance with this invention, four novel *Bt* strains, i.e., the BTS02617A, BTS02618A, BTS02654B and BTS02652E strains, are provided. The BTS02617A, BTS02618A, BTS02654B and BTS02652E crystals and crystal proteins, the BTS02618A protoxin and toxin produced by the strains during sporulation, and insecticidally effective portions of the BTS02618A protoxin, as well as equivalents of these crystals, crystal proteins, protoxin, toxin and insecticidally effective protoxin portions, each possess insecticidal activity and can therefore be formulated into insecticidal compositions against Lepidoptera in general, and particularly against Noctuidae, such as Agrotis spp. (cutworms such as *Agrotis ipsilon*), Mamestra spp. (e.g., the cabbage moth, *Mamestra brassica*) and Spodoptera spp. (armyworms, such as *Spodoptera exigua, Spodoptera frugiperda, Spodoptera littoralis* and *Spodoptera litura*), against Pyralidae (e.g., the European corn borer, *Ostrinia nubilalis*) and Yponomeutidae (such as *Plutella xylostella*) which are major pests of various economically important crops, such as corn, cotton and many vegetables such as Brassicas.

Also in accordance with this invention, a plant cell genome is transformed with the insecticidally effective bTS02618A gene part, preferably the truncated bTS02618A gene, or an equivalent thereof such as a modified, synthetic bTS02618A gene. It is preferred that this transformation be carried out with the bTS02618A chimeric gene. The resulting transformed plant cell can be used to produce transformed plants, seeds of transformed plants and plant cell cultures consisting essentially of the transformed cells. The transformed cells in some or all of the tissues of the transformed plants: 1) contain the insecticidally effective bTS02618A gene part as a stable insert in their genome, and 2) express the insecticidally effective bTS02618A gene part by producing an insecticidally effective portion of its BTS02618A protoxin, preferably its BTS02618A toxin, thereby rendering the plant resistant to Lepidoptera. The transformed plant cells of this invention can also be used to produce, for recovery, such insecticidal Bt proteins.

Further in accordance with this invention, a process is provided for rendering a plant resistant to Lepidoptera by transforming the plant cell genome with the insecticidally effective bTS02618A gene part, preferably the truncated bTS02618A gene, or an equivalent thereof. In this regard, it is preferred that the plant cell be transformed with the bTS02618A chimeric gene.

Yet further in accordance with this invention, there are provided the BTS02618A protoxin, the insecticidally effective portions of such protoxin and the BTS02618A toxin, as well as functional parts of the BTS02618A toxin, as well as the bTS02618A gene, the insecticidally effective bTS02618A gene part, the truncated bTS02618A gene and the chimeric bTS02618A gene, as well as their equivalents.

Also in accordance with this invention, a DNA sequence, either natural or artificial, encoding the BTS02618A protoxin or insecticidally effective portions thereof, such as the toxin, is provided.

Also in accordance with this invention are provided an insecticidal composition against Lepidoptera, particularly Noctuidae, Pyralidae and Yponomeutidae, and a method for controlling Lepidoptera, particularly Noctuidae, Pyralidae and Yponomeutidae, with the insecticidal composition, wherein the insecticidal composition comprises the BTS02617A, BTS02618A, BTS02654B or BTS02652E strain, crystals and/or crystal proteins or the BTS02618A protoxin, toxin and/or insecticidally effective protoxin portions or their equivalents.

DETAILED DESCRIPTION OF THE INVENTION

Figure 1:
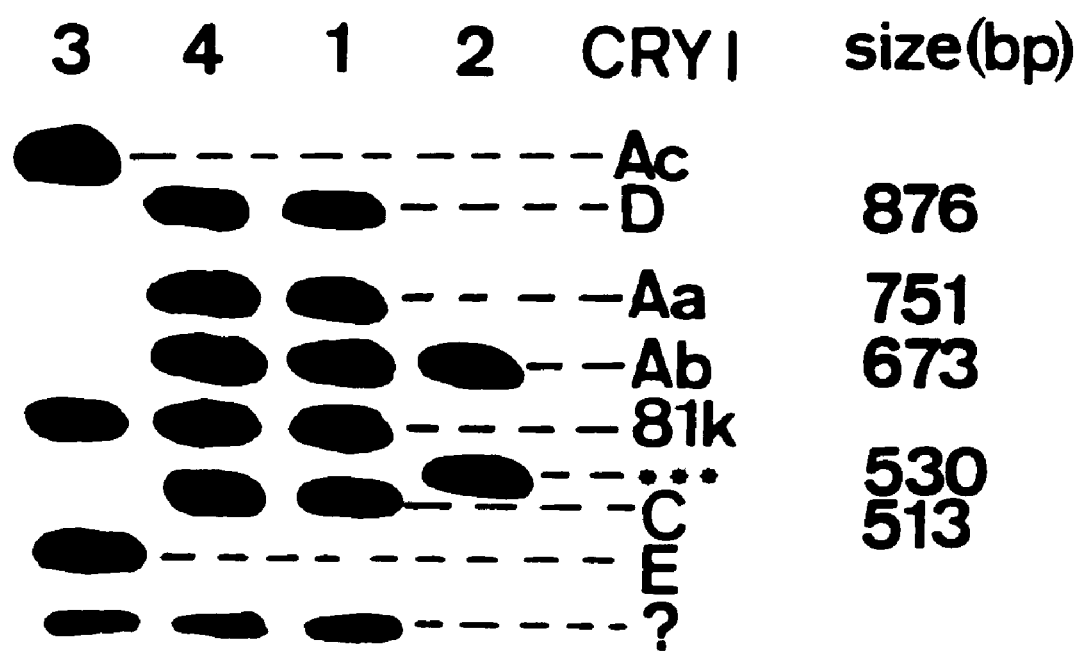

The BTS02618A protoxin of this invention can be isolated in a conventional manner from the BTS02617A strain, deposited on July, 2 at the BCCM-LMG under accession number LMG P-12592, the BTS02618A strain, deposited on Jul. 2, 1992 at the BCCM-LMG under accession number LMG P-12593, the BTS02654B strain, deposited on Jul. 2, 1992 at the BCCM-LMG under accession number LNG P-12594, or the BTS02652E strain deposited on Mar. 1, 1993 at the BCCM-LMG under accession number LMG P-13493. For example, the BTS02617A, BTS02618A, BTS02654B or BTS02652E crystals can be isolated from sporulated cultures of their respective strain (Mahillon and Delcour, 1984), and then, the BTS02618A protoxin can be isolated from the crystals according to the method of Höfte et al. (1986). The protoxins can be used to prepare monoclonal or polyclonal antibodies specific for the protoxin in a conventional manner (Höfte et al., 1988). The BTS02618A toxin can be obtained by protease (e.g., trypsin) digestion of the BTS02618A protoxin.

The bTS02618A gene can be isolated in a conventional manner. The bTS02618A gene can be identified in the BTS02617A, BTS02618A, BTS02654B or BTS02652E strain, using the procedure described in U.S. patent application Ser. No. 821,582, filed Jan. 22, 1986, and in EPA 86/300,291.1 and 88/402,115.5 (which are incorporated herein by reference). The bTS02618A gene was identified by: digesting total DNA from one of the above strains with restriction enzymes; size fractionating the DNA fragments, so produced, into DNA fractions of 5 to 10 Kb: ligating these fractions to cloning vectors; screening the *E. coli*, transformed with the cloning vectors, with a DNA probe that was constructed from a region of the cryIG gene (Smulevitch et al., 1991; Gleave et al., 1992).

The term "bTS02618A gene" as used herein includes a DNA sequence encoding the BTS02618A protoxin or toxin or functionally equivalent variants thereof. Indeed, because of the degeneracy of the genetic code, some amino acid codons can be replaced with others without changing the amino acid sequence of the protein. Furthermore, some amino acids can be substituted by other equivalent amino acids without significantly changing the insecticidal activity of the protein. Also, changes in amino acid composition in regions of the molecule, different from those responsible for binding and toxicity are less likely to cause a difference in insecticidal activity of the protein. Such equivalents of the gene include DNA sequences hybridizing to the DNA sequence of the BTS02618A toxin or protoxin of SEQ ID. No. 4 and encoding a protein with the same insecticidal characteristics as the BTS02618A (pro)toxin, of this invention. In this context, the term "hybridization" refers to conventional hybridization conditions, most preferably stringent hybridization conditions.

The term "functional parts of the BTS02618A toxin" as used herein means any part(s) or domain(s) of the toxin with a specific structure that can be transferred to another (Bt) protein for providing a new hybrid protein with at least one functional characteristic (e.g., the binding and/or toxicity characteristics) of the BTS02618A toxin (Ge et al., 1991). Such parts can form an essential feature of the hybrid *Bt* protein with the binding and/or toxicity characteristics of the BTS02618A protein. Such a hybrid protein can have an enlarged host range, an improved toxicity and/or can be used in a strategy to prevent insect resistance development (European Patent Publication ("EP") 408 403; Visser et al., 1993).

Alternatively, the 5 to 10 Kb fragments, prepared from total DNA of the BTS02617A or BTS02618A or BTS02654B or BTS02652E strain, can be ligated in suitable expression vectors and transformed in *E. coli*, and the clones can then be screened by conventional colony immunoprobing methods (French et al., 1986) for expression of the toxin with monoclonal or polyclonal antibodies raised against the BTS02618A toxin.

Also, the 5 to 10 Kb fragments, prepared from total DNA of the BTS02617A or BTS02618A or BTS02654B or BTS02652E strain, can be ligated in suitable Bt shuttle vectors (Lereclus et al., 1992) and transformed in a crystal minus Bt-mutant. The clones are then screened for production of crystals (detected by microscopy) or crystal proteins (detected by SDS-PAGE).

The so-identified bTS02618A gene was sequenced in a conventional manner (Maxam and Gilbert, 1980) to obtain the DNA sequence. Hybridization in Southern blots and sequence comparison indicated that this gene is different from previously described genes encoding protoxins and toxins with activity against Lepidoptera (Hofte and Whiteley, 1989).

An insecticidally effective part of the bTS02618A gene, encoding an insecticidally effective portion of its protoxin, and a truncated part of the gene, encoding just its toxin, can be made in a conventional manner after sequence analysis of the gene. The amino acid sequence of the BTS02618A protoxin and toxin was determined from the DNA sequence of the bTS02618A gene and the truncated bTS02618A gene. By "an insecticidally effective part" or "a part" of the bTS02618A gene is meant a DNA sequence encoding a polypeptide which has fewer amino acids than the BTS02618A protoxin but which is still toxic to Lepidoptera.

In order to express all or an insecticidally effective part of the bTS02618A gene or an equivalent gene in *E. coli*, in other Bt strains and in plants, suitable restriction sites can be introduced, flanking each gene or gene part. This can be done by site-directed mutagenesis, using well-known procedures (Stanssens et al., 1989; White et al., 1989). In order to obtain improved expression in plants, it may be preferred to modify the codon usage of the bTS02618A gene or insecticidally effective bTS02618A gene part to form an equivalent, modified or artificial gene or gene part in accordance with PCT publications WO 91/16432 and WO 93/09218; EP 0,358,962 and EP 0,359,472. For obtaining enhanced expression in monocot plants such as corn, a monocot intron also can be added to the bTS02618A chimeric gene, and the DNA sequence of the bTS02618A gene part can be further changed in a translationally neutral manner, to modify possibly inhibiting DNA sequences present in the gene part by means of site-directed intron insertion and/or by introducing changes to the codon usage, e.g., adapting the codon usage to that most preferred by the specific plant (Murray et al., 1989) without changing significantly the encoded amino acid sequence.

The insecticidally effective bTS02618A gene part or its equivalent, preferably the bTS02618A chimeric gene, encoding an insecticidally effective portion of the BTS02618A protoxin, can be stably inserted in a conventional manner into the nuclear genome of a single plant cell, and the so-transformed plant cell can be used in a conventional manner to produce a transformed plant that is insect-resistant. In this regard, a disarmed Ti-plasmid, containing the insecticidally effective bTS02618A gene part, in *Agrobacterium tumefaciens* can be used to transform the plant cell, and thereafter, a transformed plant can be regenerated from the transformed plant cell using the procedures described, for example, in EP 0,116,718, EP 0,270,822, PCT publication WO 84/02,913 and European Patent Application ("EPA") 87/400,544.0 (which are also incorporated herein by reference), and in Gould et al. (1991). Preferred Ti-plasmid vectors each contain the insecticidally effective bTS02618A gene part between the border sequences, or at least located to the left of the right border sequence, of the T-DNA of the Ti-plasmid. Of course, other types of vectors can be used to transform the plant cell, using procedures such as direct gene transfer (as described, for example in EP 0,233,247), pollen mediated transformation (as described, for example in EP 0,270,356, PCT publication WO 85/01856, and U.S. Pat. No. 4,684,611), plant RNA virus-mediated transformation (as described, for example in EP 0,067,553 and U.S. Pat. No. 4,407,956), liposome-mediated transformation (as described, for example in U.S. Pat. No. 4,536,475), and other methods such as the recently described methods for transforming certain lines of corn (Fromm et al., 1990; Gordon-Kamm et al., 1990) and rice (Shimamoto et al., 1989; Datta et al., 1990) and the recently described method for transforming monocots generally (PCT publication WO 92/09696).

The resulting transformed plant can be used in a conventional plant breeding scheme to produce more transformed plants with the same characteristics or to introduce the insecticidally effective bTS02618A gene part in other varieties of the same or related plant species. Seeds, which are obtained from the transformed plants, contain the insecticidally effective bTS02618A gene part as a stable genomic insert. Cells of the transformed plant can be cultured in a conventional manner to produce the insecticidally effective portion of the BTS02618A protoxin, preferably the BTS02618A toxin, which can be recovered for use in conventional insecticide compositions against Lepidoptera (U.S. patent application Ser. No. 821,582; EPA 86/300291.1.).

The insecticidally effective bTS02618A gene part, preferably the truncated bTS02618A gene, is inserted in a plant cell genome so that the inserted gene is downstream (i.e., 3') of, and under the control of, a promoter which can direct the expression of the gene part in the plant cell. This is preferably accomplished by inserting the bTS02618A chimeric gene in the plant cell genome. Preferred promoters include: the strong constitutive 35S promoters (the "35S promoters") of the cauliflower mosaic virus of isolates CM 1841 (Gardner et al., 1981), CabbB-S (Franck et al., 1980) and CabbB-JI (Hull and Howell, 1987); and the TR1' promoter and the TR2' promoter (the "TR1' promoter" and "TR2' promoter", respectively) which drive the expression of the 1' and 2' genes, respectively, of the T-DNA (Velten et al., 1984). Alternatively, a promoter can be utilized which is not constitutive but rather is specific for one or more tissues or organs of the plant (e.g., leaves and/or roots) whereby the inserted bTS02618A gene part is expressed only in cells of the specific tissue(s) or organ(s). For example, the insecticidally effective bTS02618A gene part could be selectively expressed in the leaves of a plant (e.g., corn, cotton) by placing the insecticidally effective gene part under the control of a light-inducible promoter such as the promoter of the ribulose-1,5-bisphosphate carboxylase small subunit gene of the plant itself or of another plant such as pea as disclosed in U.S. patent application Ser. No. 821,582 and EPA 86/300,291.1. Another alternative is to use a promoter whose expression is inducible (e.g., by temperature or chemical factors).

The insecticidally effective bTS02618A gene part is inserted in the plant genome so that the inserted gene part is upstream (i.e., 5') of suitable 3' end transcription regulation signals (i.e., transcript formation and polyadenylation signals). This is preferably accomplished by inserting the bTS02618A chimeric gene in the plant cell genome. Preferred polyadenylation and transcript formation signals include those of the octopine synthase gene (Gielen et al., 1984) and the T-DNA gene 7 (Velten and Schell, 1985), which act as 3'-untranslated DNA sequences in transformed plant cells.

The insecticidally effective bTS02618A gene part can optionally be inserted in the plant genome as a hybrid gene (EPA 86/300,291.1; Vaeck et al., 1987) under the control of the same promoter as a selectable marker gene, such as the neo gene (EP 0,242,236) encoding kanamycin resistance, so that the plant expresses a fusion protein.

All or part of the bTS02618A gene, encoding an anti-lepidopteran protein, can also be used to transform other bacteria, such as a *B. thuringiensis* which has insecticidal activity against Lepidoptera or Coleoptera. Thereby, a transformed *Bt* strain can be produced which is useful for combatting a wide spectrum of lepidopteran and coleopteran insect pests or for combatting additional lepidopteran insect pests. Transformation of bacteria with all or part of the bTS02618A gene, incorporated in a suitable cloning vehicle, can be carried out in a conventional manner, preferably using conventional electroporation techniques as described in Mahillon et al. (1989) and in PCT Patent publication WO 90/06999.

The BTS02617A, BTS02618A, BTS02654B or BTS02652E strain also can be transformed with all or an insecticidally effective part of one or more foreign *Bt* genes such as: the bt18 gene (EP 0,358,557) or another *Bt* gene coding for an anti-Lepidoptera protein; and the bt109P gene (PCT publication WO 91/16433), coding for an anti-Coleoptera protein. Thereby, a transformed *Bt* strain can be produced which is useful for combatting an even greater variety of insect pests (e.g., Coleoptera and/or additional Lepidoptera).

Transformation of the BTS02617A, BTS02618A, BTS02654B or BTS02652E strain with all or part of a foreign *Bt* gene, incorporated in a conventional cloning vector, can be carried out in a well known manner, preferably using conventional electroporation techniques (Chassy et al., 1988) or other methods, e.g., as described by Lereclus et al. (1992).

Each of the BTS02617A, BTS02618A, BTS02654B or BTS02652E strains can be fermented by conventional methods (Dulmage, 1981; Bernhard and Utz, 1993) to provide high yields of cells. Under appropriate conditions which are well understood (Dulmage, 1981), the BTS02617A, BTS02618A, BTS02654B and BTS02652E strains each sporulate to produce crystal proteins containing the BTS02168A protoxin in high yields.

An insecticidal, particularly anti-lepidopteran, composition of this invention can be formulated in a conventional manner using the BTS02617A, BTS02618A, BTS02654B or BTS02652E strain or preferably their respective crystals, crystal proteins or the BTS02168A protoxin, toxin or insecticidally effective& protoxin portion as an active ingredient, together with suitable carriers, diluents, emulsifeiers and/or dispersants (e.g., as described by Bernhard and Utz, 1993). This insecticide composition can be formulated as a wettable powder, pellets, granules or dust or as a liquid formulation with aqueous or non-aqueous solvents as a foam, gel, suspension, concentrate, etc. The concentration of the BTS02617A, BTS02618A, BTS02654B or BTS02652E strain, crystals, crystal proteins, or the BTS02618A protoxin, toxin or insecticidally effective protoxin portions in such a composition will depend upon the nature of the formulation and its intended mode of use. Generally, an insecticide composition of this invention can be used to protect a field for 2 to 4 weeks against Lepidoptera with each application of the composition. For more extended protection (e.g., for a whole growing season), additional amounts of the composition should be applied periodically.

A method for controlling insects, particularly Lepidoptera, in accordance with this invention preferably comprises applying (e.g., spraying), to a locus (area) to be protected, an insecticidal amount of the BTS02617A, BTS02618A, BTS02654B or BTS02652E strain, spores, crystals, crystal proteins or the BTS02168A protoxin, toxin or insecticidally effective protoxin portions, preferably the BTS2168A toxin. The locus to be protected can include, for example, the habitat of the insect pests or growing vegetation or an area where vegetation is to be grown.

To obtain the BTS02618A protoxin or toxin, cells of the BTS02617A, BTS02618A, BTS02654B or BTS02652E strain can be grown in a conventional manner on a suitable culture medium and then lysed using conventional means such as enzymatic degradation or detergents or the like. The protoxin can then be separated and purified by standard techniques such as chromatography, extraction, electrophoresis, or the like. The toxin can then be obtained by trypsin digestion of the protoxin.

The BTS02617A, BTS02618A, BTS02654B or BTS02652E cells can also be harvested and then applied intact, either alive or dead, preferably dried, to the locus to be protected. In this regard, it is preferred that a purified BTS02617A, BTS02618A, BTS02654B or BTS02652E strain (either alive or dead) be used, particularly a cell mass that is 90.0 to 99.9% of the BTS02617A, BTS02618A, BTS02654B or BTS02652E strain.

The BTS02617A, BTS02618A, BTS02654B, or BTS02652E cells, crystals or crystal proteins or the BTS02618 protoxin, toxin, or insecticidally effective protoxin portion can be formulated in an insecticidal composition in a variety of ways, using any number of conventional additives, wet or dry, depending upon the particular use. Additives can include wetting agents, detergents, stabilizers, adhering agents, spreading agents and extenders. Examples of such a composition include pastes, dusting powders, wettable powders, granules, baits and aerosol sprays. Other *Bt* cells, crystals, crystal proteins, protoxins, toxins, and insecticidally effective protoxin portions and other insecticides, as well as fungicides, biocides, herbicides and fertilizers, can be employed along with the BTS02617A, BTS02618A, BTS02654B or BTS02652E cells, crystals or crystal proteins or the BTS02618 protoxin, toxin or insecticidally effective protoxin portions to provide additional advantages or benefits. Such an insecticidal composition can be prepared in a conventional manner, and the amount of the BTS02617A, BTS02618A, BTS02654B or BTS02652E cells, crystals or crystal proteins or the BTS02618A protoxin, toxin or insecticidally effective protoxin portion employed depends upon a variety of factors, such as the insect pest targeted, the composition used, the type of area to which the composition is to be applied, and the prevailing weather conditions. Generally, the concentration of the BTS02618A protoxin, insecticidally effective protoxin portions or toxin will be at least about 0.1% by weight of the formulation to about 100% by weight of the formulation, more often from about 0.15% to about 0.8% by weight of the formulation.

In practice, some insects can be fed the BTS02618A protoxin, toxin, insecticidally effective protoxin portion or mixtures thereof in the protected area, that is in the area where such protoxin, toxin and/or insecticidally effective protoxin portion has been applied. Alternatively, some insects can be fed intact and alive cells of the BTS02617A, BTS02618A, BTS02654B or BTS02652E strain or transformants thereof, so that the insects ingest some of the strain's protoxin anid suffer death or damage.

The following Examples illustrate the invention. The figure and the sequence listing referred to in the Examples are as follows:
FIG. 1

Southern blot analysis of AluI-digested total DNA of *Bt* strain HD127 (lane 1), the BTS02618A strain (lane 2), *Bt* strain BTS02459 (containing cryIA(c), 81k, cryIC en cryIE, lane 3), and *Bt* strain BTS02480E (containing the same genes as HD-127, lane 4), using a mixture of DNA-probes for cryI crystal protein genes, including the cryIG probe (SEQ ID no. 1). Each band corresponds to a particular crystal protein gene. With these probes, the BTS02618A strain is found to contain the cryIA(b) gene and a novel gene, which is the bTS02618A gene, identified by an AluI fragment of approximately 530 bp, hybridizing to the cryIG probe of SEQ ID no. 1. The names of the recognized cryI genes are indicated, as well as the size of some fragments. The bTS02618A gene is indicated with three asterisks; "?" indicates an unknown gene fragment.

Sequence Listing

SEQ ID No. 1—Nucleotide sequence of the DNA probe used to isolate the bTS02618A gene. This probe is derived from part of the cryIG DNA sequence and is complementary to nucleotides 2732–2750 of the DNA sequence described by Smulevitch et al. (1991).

SEQ ID No. 2—The 5' partial nucleotide sequence of the bTS02618A gene, comprising the presumptive translation initiation codon at nucleotide position 195–197.

SEQ ID No. 3—The 3' partial nucleotide sequence of the bTS02618A gene (N: unknown nucleotide), comprising the presumptive translational stop codon at nucleotide position 1146–1148.

SEQ ID No. 4—The nucleotide sequence of the bTS02618A gene and the translated amino acid sequence of the BTS02618A protoxin. The open reading frame of the protoxin reaches from nucleotide 668 to nucleotide 4141. The translation initiation codon is at nucleotide position 668–670, the translation stop codon is at nucleotide position 4139–4141.

SEQ ID No. 5—The amino acid sequence corresponding to the coding region of the nucleotide sequence of SEQ ID No. 4.

Unless otherwise stated in the Examples, all procedures for making and manipulating recombinant DNA are carried out by the standardized procedures described in Sambrook et al., *Molecular Cloninc—A Laboratorv Manual. Second Ed.*, Cold Spring Harbor Laboratory Press, N.Y. (1989).

EXAMPLE 1

Characterization of the BTS02617A, BTS02618A, BTS02654B and BTS02652E Strains.

The BTS02617A, the BTS02618A and the BTS02654B strain were isolated from grain dust sampled in Cadlan, province of Bicol, The Philippines and were deposited at the BCCM-LMG on Jul. 2, 1992 under accession Nos. LMG P-12592, LMG P-12593 and LMG P-12594, respectively. Strain BTS02652E was also isolated from Philippine grain dust, and was deposited at the BCCM-LMG on Mar., 1, 1993 under accession No. LMG P-13493.

Each strain can be cultivated on conventional standard media, preferably $T_3$ medium (tryptone 3 g/l, tryptose 2 g/l, yeast extract 1.5 g/l, 5 mg $MnCl_2$, 0.05 M $Na_2PO_4$, pH 6.8 and 1.5% agar), preferably at 28° C. For long term storage, it is preferred to mix an equal volume of a spore-crystal suspension with an equal volume of 50% glycerol and store this at −70° C. or lyophilize a spore-crystal suspension. For sporulation, growth on $T_3$ medium is preferred for 48 hours at 28° C., followed by storage at 4° C. During its vegetative phase, each of the strains can also grow under facultative anaerobic conditions, but sporulation only occurs under aerobic conditions.

Sterilization of each strain occurs by autoclave treatment at 120° C. (1 bar pressure) for 20 minutes. Such treatment totally inactivates the spores and the BTS02617A, BTS02618A, BTS02654B, and BTS02652E protoxins. UV radiation (254 nm) also inactivates the spores.

After cultivating on Nutrient Agar ("NA", Difco Laboratories, Detroit, Mich., USA) for one day, colonies of each of the BTS02617A, BTS02618A, BTS02654B and BTS02652E strains form opaque white colonies with irregular edges. Cells of each strain (Gram positive rods of 1.7–2.4×5.6–7.7 μm) sporulate after 48 hrs cultivation at 28° C. on $T_3$ agar. The crystal proteins produced during sporulation are packaged in crystals of the BTS02617A, BTS02618A, BTS02654B, and BTS02652E strains. Quite remarkably, the crystal remains attached to the spore after sporulation.

The *Bt* serotype of the BTS02617A, BTS02618A, BTS02645B and BTS02652E strains was determined to be serotype tolworthi H9 of all these strains which was determined by conventional serotyping methods as conducted by the WHO Collaborating Center for Entomopathogenic Bacillus.

EXAMPLE 2

Insecticidal Activity of the BTS02617A, BTS02618A, BTS02654B and BTS02652E Strains and the BTS02618A protoxin against Noctuidae spp., Yponomeutidae spp. and Pvralidae spp.

Toxicity assays were performed on neonate larvae (for *Plutella xylostella*, third instar larvae were used) fed on an artificial diet layered with spore-crystal mixtures from one of the BTS02617A, BTS02618A, BTS02654B and BTS02652E strains or the BTS02618S protoxin or toxin. The artificial diet was dispensed in wells of Costar 24-well plates. Formaldehyde was omitted from the diet. 50 μl of a sample dilution was applied on the surface of the diet and dried in a laminar air flow. For $LC_{50}$ assays, the dilutions were made in a PBS-BSA buffer, and five dilutions were applied. Two larvae were placed in each well and 24 larvae were used per sample dilution. Dead and living *M. brassica, S. frugiperda, H. virescens, O. nubilalis, Plutella xylostella* and *S. exigua* larvae were counted on the fifth day, and dead and living *A. ipsilon* and *S. littoralis* larvae were counted on the sixth day. The $LC_{50}$ and $LC_{95}$ values (the concentrations required to kill respectively 50% or 95% of the insects tested, expressed in number of spore-crystals/$cm^2$ or ng (pro)toxin/$cm^2$) were calculated using Probit-analysis (Finney, 1971), and the results are set forth below.

Spodoptera littoralis

| Experiment/Strain | $LC_{50}{}^a$ | $LC_{95}{}^a$ | $FL_{min-max}{}^b$ | Slope |
|---|---|---|---|---|
| Experiment 1 | | | | |
| BTS02618A | 2.4 | 7.7 | 1.5–3.4 | 3.2 |
| HD127[c] | 2.5 | 168 | 1.2–7.4 | 1.0 |
| Experiment 2 | | | | |
| BTS02618A | 1.1 | 4 | 0.8–1.6 | 3.0 |
| HD127 | 21.2 | 133.7 | 14.4–31.9 | 2.0 |

[1] $10^5$ spore-crystals per $cm^2$
[b] 95% fiducial limits of $LC_{50}$ values
[c] from the Howard Dulmage collection, housed at the Northern Region Research Center, 1815 North University, Peoria, Ill, USA. The curator is Dr. L. Nakamura.

Experiments with purified BTS02618A protoxin also show a significant toxicity of this protoxin against *S. littoralis* larvae.

Spodoptera exigua

1. Crystal/spore mixtures

| Experiment/Strain | $LC_{50}{}^a$ | $LC_{95}{}^a$ | $FL_{min-max}{}^b$ | Slope |
|---|---|---|---|---|
| Experiment 1 | | | | |
| BTS02618A | 1.4 | 7.9 | 0.48–3.9 | 2.2 |
| HD127 | 8.2 | 163.5 | 5.1–15.7 | 1.3 |
| Experiment 2 | | | | |
| BTS02618A | 1.2 | 3.56 | 0.91–1.57 | 3.5 |
| BTS02617A | 0.79 | 2.12 | 0.61–1.03 | 3.81 |
| HD127 | 3.5 | 44.2 | 1.36–11.5* | 1.5 |
| Florbac | 4.1 | 53.9 | 1.5–17.0* | 1.47 |
| BTS00170U[c] | 5.1 | 46.5 | 1.83–24.4* | 1.71 |
| Experiment 3 | | | | |
| Javelin[d] | 23.12 | 195.7 | 14.6–56.7 | 1.77 |
| Experiment 4 | | | | |
| BT502618A | 1.07 | 2.91 | 0.83–1.39 | 3.8 |
| BTS02617A | 0.87 | 4.7 | 0.59–1.21 | 2.22 |
| HD127 | 4.7 | 56.9 | 1.85–18.7* | 1.52 |
| Florbac[e] | 2.53 | 48.1 | 0.79–6.71* | 1.29 |
| BTS00170U | 1.94 | 56.3 | 0.55–5.4* | 1.12 |

[a] $10^5$ spore-crystals per $cm^2$
[b] 95% fiducial limits of $LC_{50}$ values, values marked with * are 90% fiducial limits of $LC_{50}$ values
[c] PCT patent publication WO 90/06999
[d] strain isolated from Javelin ® (Sandoz, Lichtstrasse, Basel, Switzerland)
[e] strain from Florbac ® (Novo Nordisk, Novo Alle, Bagsvaerd, Denmark)

2. Toxin/protoxin assays.

| ICP | | $LC_{50}{}^a$ | $LC_{95}{}^a$ | $FL_{min-max}{}^b$ | Slope |
|---|---|---|---|---|---|
| BTS02618A | Protoxin | 26.6 | 100.6 | 20.9–33.9 | 2.8 |
| CryIC | Toxin | 68.9 | 313.2 | 50.5–94.1 | 2.5 |
| CryID | Toxin | 118.6 | 870.6 | 82.7–170.0 | 1.9 |

[a] $ng/cm^2$
[b] 95% fiducial limits of $LC_{50}$ values

Mamestra brassica

1. Crystal/spore mixtures.

| Experiment/Strain | $LC_{50}{}^a$ | $LC_{95}{}^a$ | $FL_{min-max}{}^b$ | Slope |
|---|---|---|---|---|
| HD127 | 37.8 | 297.6 | 17.8–91.1 | 1.8 |
| BTS02618A | 8.6 | 59.6 | 6.0–12.2 | 1.9 |
| BTS02617A | 5.2 | 25.8 | 3.7–7.1 | 2.4 |
| BTS02652E | 12.9 | 44.2 | 9.7–17.2 | 3.0 |
| BTS02654B | 14.2 | 60.5 | 10.8–19.9 | 2.6 |

[a] $10^5$ spore-crystals per $cm^2$
[b] 95% fiducial limits of $LC_{50}$ values

2. Protoxin assays.

| ICP | | $LC_{50}{}^a$ | $LC_{95}{}^a$ | $FL_{min-max}{}^b$ | Slope |
|---|---|---|---|---|---|
| BTS02618A | Protoxin | 25.3 | 125.1 | 19.3–33.2 | 2.4 |
| CryIC | Protoxin | 22.0 | 62.9 | 16.3–29.6 | 3.6 |
| CryIA(b) | Protoxin | 162.4 | 7169 | 93.2–283.1 | 1.0 |

[a] $ng/cm^2$
[b] 95% fiducial limits of $LC_{50}$ values

Agrotis ipsilon

1. Crystal/spore mixtures.

| Strain | mortality[a] | genes[b] |
|---|---|---|
| Btgall.[c] | 1/20 | cryIF, cryIG, cryII, 81k |
| HD127[d] | 2/20 | cryIAa, cryIAb, cryIC, cryID, cryII, 81k |
| BTS02618A | 16/20[e] | cryIAb, cryII, bTS02618A |
| Buffer | 1/20 | none |

[a] number of 1st instar larvae killed after 6 days ($10^7$ spore-crystals per $cm^2$)
[b] genes known to be present in these strains
[c] Btgall. as described by Smulevitch et al (1991)
[d] HD127 is avallable at the Howard Dulmage Collection (NRRC, see above)
[e] surviving larvae show severe growth-inhibition

| STRAIN | $LC_{50}{}^a$ | $LC_{95}{}^a$ | $FL_{min-max}{}^b$ | Slope |
|---|---|---|---|---|
| BTS02618A | 84.4 | 207.9 | 65.9–109.6 | 4.2 |
| HD127 | >250 | | | |
| BTS02617A | 53.4 | 261.0 | 27.7–112.3 | 2.4 |

[a] $10^6$ spores/$cm^2$
[b] 95% fiducial limits of $LC_{50}$ values

2. Toxin/protoxin assay.

| ICP | | $LC_{50}{}^a$ | $LC_{95}{}^a$ | $FL_{min-max}{}^b$ | Slope |
|---|---|---|---|---|---|
| CryIAc | Toxin | >1350 | | | |
| BTS02618A | Protoxin | 212.2 | 1973 | 168.1–267.9 | 1.7 |

[a] $ng/cm^2$
[b] 95% fiducial limits of $LC_{50}$ values

Since MacIntosh et al. (1990) described some activity of the CryIAc toxin towards *A. ipsilon*, purified CryIAc toxin was tested on this insect for comparison but did not cause any significant mortality of *A. ipsilon*.

Heliothis virescens

1. Crystal/spore mixture.

| Experiment/Strain | $LC_{50}{}^a$ | $LC_{95}{}^a$ | $FL_{min-max}{}^b$ | Slope |
|---|---|---|---|---|
| BTS02617A | 1.69 | 14.99 | 0.67–2.89 | 1.73 |
| BTS02618A | 2.71 | 25.4 | 0.88–6.99 | 1.69 |
| BTS00170U[c] | 15.1 | 398.7 | 8.3–41.2 | 1.15 |
| Dipeld | 2.99 | 14.11 | 1.25–7.76 | 2.45 |

[a] $10^3$ spore-crystals per $cm^2$
[b] 95% fiducial limits of $LC_{50}$ values
[c] PCT patent publication WO 90/06999
[d] strain isolated from Dipel ™ (Abbott Laboratories, North Chicago, Ill., USA)

-continued

2. Toxin/protoxin assay.

| ICP | | $LC_{50}{}^a$ | $FL_{min-max}{}^b$ | $LC_{95}{}^a$ | Slope |
|---|---|---|---|---|---|
| BTS02618A | Protoxin | 31.6 | 20–50 | 182.7 | 2.1 |
| CryIAb | Toxin | 7.2 | 4.9–10.51 | 169.1 | 1.2 |

[a] ng/cm$^2$
[b] 95% fiducial limits of $LC_{50}$ values

*Ostrinia nubilalis*

1. Crystal/spore mixtures.

| Experiment/Strain | $LC_{50}{}^a$ | $LC_{95}{}^a$ | $FL_{min-max}{}^b$ | Slope |
|---|---|---|---|---|
| BTS02617A | 4.92 | 12.49 | 2.45–6.81 | 4.0 |
| BTS02618A | 6.17 | 39.7 | 2.93–9.74 | 2.0 |
| Dipel[c] | >30 | | | |

[a] 10$^5$ spore-crystals per cm$^2$
[b] 95% fiducial limits of $LC_{50}$ values
[c] strain isolated from Dipel ™ (Abbott Laboratories)

2. Purified protoxin assay

| ICP | | 100% Mortality[a] |
|---|---|---|
| CryIAb | Toxin | 1350 |
| CryIB | Toxin | 1350 |
| BTS02618A | Protoxin | 100 |

[a] concentration at which 100% mortality was observed (in ng/cm$^2$)

The purified BTS02618A protoxin also showed a significant toxicity to *Ostrinia nubilalis* larvae, as compared with the CryI toxins that are most active against Ostrinia.

*Plutella xylostella*

*Plutella xylostella* larvae also showed significant mortality after application of purified BTS02618A toxin to their artificial diet in several experiments.

*Spodoptera frugiperda*

Crystal/spore mixtures of a bTS02618A gene-transformed crystal-minus *Bt* strain (Mahillon et al., 1989) were also found to significantly inhibit larval growth of *S. frugirerda* larvae in insect feeding trials.

In conclusion, the strains of this invention and the BTS02618A protein of this invention have a strong insecticidal activity against a broad range of insects that are not susceptible to any single currently available *Bt* protein and have an activity against at least three Spodontera spp. and against other Noctuidae, such as *A. ipsilon*, *M. brassica* and *H. virescens*, as well as against Pyralidae, such as *O. nubilalis* and Yponomeutidae such as *Plutella xylostella*. These results are summarized and compared with results for other CryI genes (Van Frankenhuyzen, 1993) in Table 1 which shows the unique range of insects susceptible to the BTS02618A protein.

EXAMPLE 3

Identification of the bTS02618A gene

The bTS02618A gene was identified in the BTS02618A strain by Southern blot analysis (FIG. 1) of AluI digested total DNA of the strain using, as a DNA probe, the DNA sequence of the cryIG gene (Gleave et al., 1992) of SEQ ID No. 1 and using standard hybridization conditions. Partial DNA sequences of the bTS02618A gene, showing its 5' and 3' end portions, are shown in SEQ ID Nos. 2 and 3, respectively, and the full DNA sequence of the bTS02618A gene and the full amino acid sequence of the BTS02618A protein are shown in SEQ ID No. 4.

The partial sequences of SEQ ID Nos. 2 and 3 allow the bTS02618A gene to be recognized in the BTS02617A, BTS02654B and BTS02652E strains and allow the construction of probes to identify and isolate the full gene sequence in these and other *Bt* strains. The translation initiation codon of the bTS02618A gene is identified at nucleotide position 195–197 in SEQ ID No. 2, corresponding to nucleotide position 668–670 in SEQ ID No.4. The translation stop codon is identified at nucleotide position 1146–1148 in SEQ ID No. 3, corresponding to nucleotide position 4139–4141 in SEQ ID No. 4.

The bTS02618A gene was also identified in the BTS02617A, BTS02654B and BTS02652E strains by using the DNA sequence of SEQ ID No. 1 as a probe, as well as other DNA probes of conserved DNA fragments in cryI genes.

The full length bTS02618A gene was found to encode a 129.9 kD protoxin. A comparison of the amino acid sequence with other known CryI proteins showed that the C-terminal part (C-terminal of conserved sequence block 5) was homologous with CryIG (88%). The best homology for the N-terminal part (the toxin) was found with the CryIB toxin, but this was found to be less than 50% (homology is expressed as the number of perfect matches divided by the number of amino acids of the longest fragment).

The smallest insecticidal protein is believed to be a 69 kD (615 amino acids) protein stretching from amino acid number 44 to amino acid number 658 in SEQ ID No. 4. A smaller tryptic fragment of 55 kD (494 amino acids), stretching from amino acid number 165 to amino acid number 658 in SEQ ID No. 4, still has insecticidal activity towards *S. exigua*, but this activity is significantly reduced. Thus, a truncated bTS02618A gene or an equivalent truncated gene preferably encodes the 69 kD protein of the BTS02618A protoxin of SEQ ID No.4 as described above.

EXAMPLE 4

Cloning and expression of the bTS02618A Gene

In order to isolate the bTS02618A gene, total DNA from the BTS02618A strain was prepared and partially digested with Sau3A. The digested DNA was size fractionated on a sucrose gradient and fragments ranging from 7 Kb to 10 Kb were ligated to the BamHI-digested and BAP-treated cloning vector pUC19 (Yannisch-Perron et al., 1985). Recombinant *E.coli* clones containing the vector were then screened with the cryIG DNA probe of SEQ ID No. 1 which is described in Example 3, to identify clones containing the bTS02618A gene.

The so-identified DNA fragments were then sequenced according to Maxam and Gilbert (1980). Partial sequences of the bTS02618A gene are shown in SEQ ID Nos. 2 and 3, and a full sequence of the bTS02618A gene and the BTS02618A protein is shown in SEQ ID No. 4. Based on the DNA sequence analysis, the gene is cut with appropriate restriction enzymes to give the truncated bTS02618A gene encoding the BTS02618A toxin. Expression of the gene in *E.coli* was induced using standard procedures (Sambrook et al., 1989, supra).

The bTS02618A gene is also introduced by routine procedures into a crystal-minus *Bt* strain, using *Bt* plasmids PGI2 or PGI3 (Mahillon and Seurinck 1988; Mahillon et al., 1988).

EXAMPLE 5

Insertion of the bTS02618A Gene and the Truncated bTS02618A Gene in *E. coli* and Insertion of the Truncated bTS02618A Gene in Plants.

In order to express the bTS02618A gene and the truncated bTS02618A gene of Example 4 in *E. coli* and in plants, different gene cassettes are made in *E. coli* according to the procedure described in EPA 86/300291.1 and EPA 88/402115.5.

To allow significant expression in plants, cassettes containing a) the truncated gene or b) a hybrid gene that is a fusion of i) the truncated gene and ii) the neo gene are each:

inserted between the T-DNA border sequences of intermediate plant expression vectors as described in EPA 86/300291.1; fused to transcript formation and polyadenylation signals in the plant expression vectors; placed under the control of the constitutive promoter from cauliflower mosaic virus driving the 35S3 transcript (Hull and Howell, 1987) or the 2' promoter from the TR-DNA of the octopine Ti-plasmid (Velten et al., 1984); and fused to 3' end transcript formation and polyadenylation signals of the octopine synthase gene (Gielen et al., 1984).

Using standard procedures (Deblaere et al., 1985), the intermediate plant expression vectors, containing the truncated bTS02618A gene, are transferred into the Agrobacterium strain C58C1Rif® (U.S. patent application Ser. No. 821,582; EPA 86/300,291.1) carrying the disarmed Ti-plasmid pGV2260 (Vaeck et al., 1987). Selection for spectinomycin resistance yields cointegrated plasmids, consisting of pGV2260 and the respective intermediate plant expression vectors. Each of these recombinant Agrobacterium strains is then used to transform different cotton plants so that the truncated bTS02618A gene is contained in, and expressed by, different plant cells.

EXAMPLE 6

Expression of the Truncated bTS02618A Gene in Plants.

The insecticidal activity against Lepidoptera of the expression products of the truncated bTS02618A gene in leaves of transformed plants, generated from the transformed plant cells of Example 5, is evaluated by recording the growth rate and mortality of Agrotis and Spodoptera spp. larvae fed on these leaves. These results are compared with the growth rate of larvae fed leaves from untransformed plants. Toxicity assays against Agrotis and Spodoptera spp. are performed as described in EP 0,358,557, U.S. patent application Ser. No. 821,582 and EPA 86/300,291.1. A significantly higher mortality rate is obtained among larvae fed on leaves of transformed plants containing the truncated bTS02618A gene and the truncated bTS02618A-neo hybrid gene than among larvae fed the leaves of untransformed plants. The transformed plants are also found to resist *Ostrinia nubilalis Mamestra brassica, Heliothis virescens* and *Plutella xylostella* attack by their expression of the BTS02618A protein.

Needless to say, this invention is not limited to the BTS02617A strain (BCCM-LMG P-12592), the BTS02618A strain (BCCM-LMG P-12593), the BTS02654B strain (BCCM-LMG P-12594) and the BTS02652E (BCCM-LMG P-13493) strain. Rather, the invention also includes any mutant or variant of the BTS02617A, BTS02618A, BTS02654B, and BTS02652E strain which produces crystals, crystal proteins, protoxin or toxin having substantially the same properties, particularly anti-Lepidoptera properties, quite particularly anti-Noctuidae, anti-Yponomeutidae and anti-Pyralidae properties, especially anti-Spodoitera, anti-Plutella, anti-Ostrinia anti-Mamestra; anti-Heliothis and anti-Agrotis properties, as the respective BTS02617A, BTS02618A, BTS02654B or BTS02652E crystals or crystal proteins, or the BTS02618A protoxin or toxin. This invention also includes the bTS02618A gene and any insecticidally effective parts thereof, like the truncated bTS02618A gene. In this regard, the term “bTS02618A gene” as used herein means the gene isolated from the BTS02617A, BTS02618A, BTS02654B or BTS02652E strain and hybridizing to the nucleotide sequence of SEQ ID No. 1 and any equivalent gene encoding a protoxin having substantially the same amino acid sequence and insecticidal activity as the BTS02618A protoxin and preferably containing the partial nucleotide sequences shown in SEQ ID Nos. 2 and 3, or the full sequence shown in SEQ ID No. 4.

This invention also is not limited to cotton plants transformed with the truncated bTS02618A gene. It includes any plant, such as tomato, tobacco, rapeseed, alfalfa, sunflower, lettuce, potato, corn, rice, soybean, Brassica species, sugar beet and other legumes and vegetables, transformed with an insecticidally effective part of the bTS02618A gene or an equivalent gene.

Nor is this invention limited to the use of *Agrobacterium tumefaciens* Ti-plasmids for transforming plant cells with an insecticidally effective bTS02618A gene part. Other known techniques for plant cell transformations, such as by means of liposomes, by electroporation or by vector systems based on plant viruses or pollen, can be used for transforming monocotyledons and dicotyledons with such a gene part.

Furthermore, DNA sequences other than those present naturally in the BTS02617A, BTS02618A, BTS02654B and BTS02652E strains and encoding the BTS02618A protoxin and toxin can be used for transforming plants and bacteria. In this regard, the natural DNA sequence of these genes can be modified by: 1) replacing some codons with others that code either for the same or different, preferably the same, amino acids; 2) deleting or adding some codons; and/or 3) reciprocal recombination as described by Ge et al. (1991); provided that such modifications do not substantially alter the properties, particularly the insecticidal properties, especially anti-lepidoptera properties, of the encoded, insecticidally effective portions of the BTS02618A protoxin (e.g., toxin). For example, an artificial bTS02618A gene or gene part of this invention, as described above, having a modified codon usage, could be used in certain circumstances instead of a natural insecticidally effective bTS02618A gene part in a bTS02618A chimeric gene of this invention for transforming plants.

Also, other DNA recombinants containing all or part of the bTS02618A gene in association with other foreign DNA, particularly the DNA of vectors suitable for transforming plants and microorganisms other than *E. coli*, are encompassed by this invention. In this regard, this invention is not limited to the specific plasmids containing the bTS02618A gene, or parts thereof, that were heretofore described, but rather, this invention encompasses any DNA recombinants containing DNA sequences that are their equivalent. Further, the invention relates to all DNA recombinants that include all or part of the bTS02618A gene and that are suitable for transforming microorganisms (e.g., plant associated bacteria such as other *Bacillus thurinciensis* strains, *Bacillus subtilis*, Pseudomonas, and Xanthomonas or yeasts such as *Streptomyces cerevisiae*) under conditions which enable all or part of the gene to be expressed and to be recoverable from said microorganisms or to be transferred to a plant cell.

TABLE 1

Activity of CryI proteins towards several lepidopteran insect pests: + and − indicates the presence or absence of insecticidal activity, +/− indicates low activity (according to Van Frankenhuyzen (1993)), NA indicates no data available, the protein BTS02618A is abbreviated as 2618A (data of Van Frankenhuyzen (1993) and this invention (for *A. ipsilon* and 2618A)).

| | 2618A | IAb | IAc | IB | IC | IF |
|---|---|---|---|---|---|---|
| *S. exigua* | + | +/− | − | − | + | + |
| *S. littoralis* | + | − | − | − | + | NA |
| *H. virescens* | + | + | + | − | +/− | + |
| *A. ipsilon* | + | NA | − | NA | NA | NA |
| *O. nubilalis* | + | + | + | NA | NA | + |
| *P. xylostella* | + | + | + | + | + | NA |
| *M. brassica* | + | + | − | − | + | NA |

References

Berhard, K. and Utz, R., “Production of *Bacillus thuringiensis* insecticides for experimental and commercial uses”, In *Bacillus thuringiensis*, An Environmental Biopesticide:

Theory and Practice, pp.255–267, eds. Entwistle, P. F., Cory, J. S., Bailey, M. J. and Higgs, S., John Wiley and Sons, New York (1993).

Chassy, B. M., Mercenier, A. and Flickinger, J., Trends Biotechnol. 6, 303–309 (1988).

Datta S., Peterhans A., Datta K. and Potrykus I., Bio/Technology 8, 736–740 (1990).

Deblaere, R., Bijtebier, B. De Greve , H., Debock, F., Schell, J., Van Montagu, M. and Leemans, J., Nucleic Acids Research 13, 4777–4788 (1985).

Dulmage, H. T., "Production of Bacteria for Biological Control of Insects" in *Biological Control in Crop Production*, Ed. Paparizas, D.C., Osmun Publishers, Totowa, N.J., USA, pp. 129–141 (1981).

Finney, Probit Analysis, 3rd Edition, Cambridge University Press (1971)

Franck, Guilley, Jonard, Richards and Hirth, Cell 21, 285–294 (1980)

French, B. T., Maul, H. N. and Maul, G. G., Anal.Biochem. 156, 417–423 (1986)

Fromm M., Morrish F., Armstrong C., Williams R., Thomas J. and Klein T., Bio/Technology 8, 833–839 (1990).

Gardner, Howarth, Hahn, Brown-Luedi, Shepard and Messing, Nucleic Acids Research 9, 2871–2887 (1981)

Ge A., Rivers D., Milne R. and Dean D., J. Biol. Chem. 266, 17954–17958 (1991)

Gielen, J., De Beukeleer, M., Seurinck, J., Deboeck, F., De Greve, H., Lemmers, M., Van Montagu, M. and Schell, J., EMBO J 3, 835–845 (1984).

Gleave, A. P., Hegdes, R. J. and Broadwell, A. H., J. Gen. Microbiol. 138, 55–62 (1992).

Gordon-Kamm W., Spencer M., Mangano M., Adams T., Daines R., Start W., O'Brien J., Chambers S., Adams W., Willets N., Rice T., Mackey C., Krueger R., Kausch A. and Lemaux P., The Plant Cell 2, 603–618 (1990).

Gould, J., Devey, M., Hasegawa, O., Ulian, E. C., Peterson, G. and Smith, R. H., Plant Physiol. 95, 426–434 (1991).

Höfte, H., De Greve, H., Seurinck, J., Jansens, S., Mahillon, J., Ampe, Vandekerckhove, J, Vanderbruggen, H., Van Montagu, M., Zabeau, M. and Vaeck, M., Eur. J. Biochem. 161, 273–280 (1986)

Höfte, H., Van Rie, J., Jansens, S., Van Houtven, A., Verbruggen, H. and Vaeck, M., Applied and Environmental Microbiology 54, 2010–2017 (1988)

Höfte H. and Whiteley H. R., Microbiological Review 53, 242–255 (1989).

Hull and Howell, Virology 86, 482–493 (1987)

Lereclus, D.; Vallade, M.; Chaufaux, J.; Arantes, O. & Rambaud, S., Bio/Technology 10, 418 (1992).

MacIntosh, S. C. et al, J. Invertebrate Patholog. 56, 258–266 (1990).

Mahillon, J. and Delcour, J., J. Microbiol. Methods 3, 69–73 (1984).

Mahillon, J. and Seurinck, J., Nucl. Acids Res. 16, 11827–11828 (1988).

Mahillon et al, Plasmid 19, 169–173 (1988).

Mahillon et al, FEMS Microbiol. Letters 60, 205–210 (1989).

Maxam, A. M. and Gilbert, W., Methods in Enzymol. 65, 499–560 (1980).

Murray, E., Lotzer, J. and Eberle, M., Nucleic Acids Research 17(2), 477–498 (1989).

Shimamoto K., Terada R., Izawa T. and Fujimoto H., Nature 338, 274–276 (1989).

Smulevitch, S. V., Osterman, A. L., Shevelev, A. B., Kaluger, S. V., Karasin, A. I., Kadyrov, R. M., Zagnitko, O. P., Chestukhina, G. G. and Stepanov, V. M., FEBS Lett. 293, 1(2), 25–28 (1991).

Stanssens P., Opsomer C., McKeown Y., Kramer W., Zabeau M. and Fritz H. J., Nucleic Acids Research 12, 4441–4454 (1989).

Vaeck, M., Reynaerts, A., Höfte, H., Jansens, S., De Beuckeleer, M., Dean, C., Zabeau, M., Van Montagu, M. and Leemans, J., Nature 327, 33–37(1987).

Van Frankenhuyzen, "The Challenge of *Bacillus thuringiensis*", in "*Bacillus thuringiensis*, An Environmental Biopesticide: Theory and Practice", pp.1–35, eds. Entwistle, P. F., Cory, J. S., Bailey, M. J. and Higgs, S., John Wiley and Sons, New York (1993).

Velten, J., Velten, L., Hain, R. and Schell, J., EMBO J 3, 2723–2730 (1984).

Velten, J. and Schell, J. Nucleic Acids Research 13, 6981–6998 (1985)

Visser, B., Bosch, D. and Honee, G., "Domain-Structure Studies of *Bacillus thurinciensis* Crystal Proteins: A Genetic Approach", In *Bacillus thurinaiensis*, An Environmental Biopesticide: Theory and Practice, pp.71–88, eds. Entwistle, P. F., Cory, J. S., Bailey, M. J. and Higgs, S., John Wiley and Sons, New York (1993).

Yannisch-Perron, C., Vierra, J. and Messing, J., Gene 33, 103–119 (1985).

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: other nucleic acid
      (A) DESCRIPTION:   /desc = "synthetic DNA"

(ix) FEATURE:
            (A) NAME/KEY: misc_feature
            (B) LOCATION:1..19
            (D) OTHER INFORMATION:/function= "for isolating bTS02618A
                gene from its containing strain"
                /note= "the probe is a part of the coding DNA strand of
                the cryIG gene (Smulevitch et al. (1991)"

(ix) FEATURE:
            (A) NAME/KEY: misc_feature
            (B) LOCATION:1..19
            (D) OTHER INFORMATION:/note= "this probe is used to
                isolate the bTS02618A gene from its containing strain"

(xi) SEQUENCE DESCRIPTION: SEQ ID NO: 1:

TTCTGTACTA TTGATTGTA                                                    19

(2) INFORMATION FOR SEQ ID NO: 2:

(i) SEQUENCE CHARACTERISTICS:
            (A) LENGTH: 1561 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Bacillus thuringiensis
            (B) STRAIN: BTS02618A (ix) FEATURE:
            (A) NAME/KEY: misc_feature
            (B) LOCATION:1..1561
            (D) OTHER INFORMATION:/note= "contains the translation
                initiation codon of the bTS02618A gene"

(xi) SEQUENCE DESCRIPTION: SEQ ID NO: 2:

AAAAGAAAT AGGAATAAAT ACTATCCATT TTTTCAAGAA ATATTTTTTT ATTAGAAAGG         60

AATCTTTCTT ACACGGGAAA ATCCTAAGAT TGAGAGTAAA GATATATATA TATAAATACA 120

ATAAAGAGTT TGTCAGGATT TTTGAAAGAT ATGATATGAA CATGCACTAG ATTTATAGTA 180

TAGGAGGAAA AAGTATGAAT CGAAATAATC AAAATGAATA TGAAATTATT GATGCCCCCC 240

ATTGTGGGTG TCCATCAGAT GACGATGTGA GGTATCCTTT GGCAAGTGAC CCAAATGCAG 300

CGTTACAAAA TATGAACTAT AAAGATTACT TACAAATGAC AGATGAGGAC TACACTGATT 360

CTTATATAAA TCCTAGTTTA TCTATTAGTG GTAGAGATGC AGTTCAGACT GCGCTTACTG 420

TTGTTGGGAG AATACTCGGG GCTTTAGGTG TTCCGTTTTC TGGACAAATA GTGAGTTTTT 480

ATCAATTCCT TTTAAATACA CTGTGGCCAG TTAATGATAC AGCTATATGG GAAGCTTTCA 540

TGCGACAGGT GGAGGAACTT GTCAATCAAC AAATAACAGA ATTTGCAAGA AATCAGGCAC 600

TTGCAAGATT GCAAGGATTA GGAGACTCTT TTAATGTATA TCAACGTTCC CTTCAAAATT 660

GGTTGGCTGA TCGAAATGAT ACACGAAATT TAAGTGTTGT TCGTGCTNAA TTTATAGCTT 720

TAGACCTTGA TTTTGTTAAT GCTATTCCAT TGTTTGCAGT AAATGGACAG CAGGTTCCAT 780

TACTGTCAGT ATATGCACAA GCTGTGAATT TACATTTGTT ATTATTAAAA GATGCATCTC 840

TTTTTGGAGA AGGATGGGGA TTCACACAGG GGGAAATTTC CACATATTAT GACCGTCAAT 900

TGGAACTAAC CGCTAAGTAC ACTAATTACT GTGAAACTTG GTATAATACA GGTTTAGATC 960

GTTTAAGAGG AACAAATACT GAAAGTTGGT TAAGATATCA TCAATTCCGT AGAGAAATGA 1020

-continued

```
CTTTAGTGGT ATTAGATGTT GTGGCGCTAT TTCCATATTA TGATGTACGA CTTTATCCAA   1080

CGGGATCAAA CCCACAGCTT ACACGTGAGG TATATACAGA TCCGATTGTA TTTAATCCAC   1140

CAGCTAATGT TGGACTTTGC CGACGTTGGG GTACTAATCC CTATAATACT TTTTCTGAGC   1200

TCGAAAATGC CTTCATTCGC CCACCACATC TTTTTGATAG GCTGAATAGC TTAACAATCA   1260

GCAGTAATCG ATTTCCAGTT TCATCTAATT TTATGGATTA TTGGTCAGGA CATACGTTAC   1320

GCCGTAGTTA TCTGAACGAT TCAGCAGTAC AAGAAGATAG TTATGGCCTA ATTACAACCA   1380

CAAGAGCAAC AATTAATCCC GGAGTTGATG GAACAAACCG CATAGAGTCA ACGGCAGTAG   1440

ATTTTCGTTC TGCATTGATA GGTATATATG GCGTGAATAG AGCTTCTTTT GTCCCAGGAG   1500

GCTTGTTTAA TGGTACGACT TCTCCTGCTA ATGGAGGATG TAGAGATCTC TATGATACAA   1560

A                                                                   1561
```

(2) INFORMATION FOR SEQ ID NO: 3:

(i) SEQUENCE CHARACTERISTICS:
(A) LENGTH: 1554 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Bacillus thuringiensis
(B) STRAIN: BTS02618A (ix) FEATURE:
(A) NAME/KEY: misc_feature
(B) LOCATION:1146..1148
(D) OTHER INFORMATION:/note= "Presumed translational stop codon of bTS02618A gene"

(xi) SEQUENCE DESCRIPTION: SEQ ID NO: 3:

```
AAAATTATCC AACATACATT TATCAAAAAG TAGATGCATC GGTGTTAAAG CCTTATACAC     60

GCTATAGACT AGATGGATTT GTGAAGAGTA GTCAAGATTT AGAAATTGAT CTCATCCACC    120

ATCATAAAGT CCATCTTGTA AAAAATGTAC CAGATAATTT AGTATCTGAT ACTTACTCAG    180

ATGGTTCTTG CAGCGGAATC AACCGTTGTG ATGAACAGCA TCAGGTAGAT ATGCAGCTAG    240

ATGCGGAGCA TCATCCAATG GATTGCTGTG AAGCGGCTCA AACACATGAG TTTTCTTCCT    300

ATATTAATAC AGGGGATCTA AATGCAAGTG TAGATCAGGG CATTTGGGTT GTATTAAAAG    360

TTCGAACAAC AGATGGGTAT GCGACGTTAG GAAATCTTGA ATTGGTAGAG GTTGGGCCAT    420

TATCGGGTGA ATCTCTAGAA CGGGAACAAA GAGATAATGC GAAATGGAAT GCAGAGCTAG    480

GAAGAAAACG TGCAGAAATA GATCGTGTGT ATTTAGCTGC GAAACAAGCA ATTAATCATC    540

TGTTTGTAGA CTATCAAGAT CAACAATTAA ATCCAGAAAT TGGGCTAGCA GAAATTAATG    600

AAGCTTCAAA TCTTGTAGAG TCAATTTCGG GTGTATATAG TGATACACTA TTACAGATTC    660

CTGGGATTAA CTACGAAATT TACACAGAGT TATCCGATCG CTTACAACAA GCATCGTATC    720

TGTATACGTC TAGAAATGCG GTGCAAAATG GAGACTTTAA CAGTGGTCTA GATAGTTGGA    780

ATACAACTAT GGATGCATCG GTTCAGCAAG ATGGCAATAT GCATTTCTTA GTTCTTTCGC    840

ATTGGGATGC ACAAGTTTCC CAACAATTGA GAGTAAATCC GAATTGTAAG TATGTCTTAC    900

GTGTGACAGC AAGAAAAGTA GGAGGCGGAG ATGGATACGT CACAATCCGA GATGGCGCTC    960
```

-continued

```
ATCACCAAGA AACTCTTACA TTTAATGCAT GTGACTACGA TGTAAATGGT ACGTATGTCA      1020

ATGACAATTC GTATATAACA GAAGAAGTGG TATTCTACCC AGAGACAAAA CATATGTGGG      1080

TAGAGGTGAG TGAATCCGAA GGTTCATTCT ATATAGACAG TATTGAGTTT ATTGAAACAC      1140

AAGAGTAGAA GAGGGGATC CTAACGTATA GCAACTATGA GAGGATACTC CGTACAAACA       1200

AAGATTAAAA AAAGGTAAAA TGAATAGAAC CCCCTACTGG TAGAAGGACC GATAGGGGGT     1260

TCTTACATGA AAAAATGTAG CTGTTTACTA AGGTGTATAA AAAACAGCAT ATCTGATAGA     1320

AAAAAGTGAG TACCTTATAA AGAAAGAATT CCATTCACAG TTTCGGTATC ATATAAATAA     1380

TGATAGGGGT ATCCTTCTTA TTTACATTAT TTTTCGCAAT TATCTCGACG TTCTTCTTTC     1440

CGCTCACAAT GATGATGATC ATGACAACAA TCGCGTCCAT AGCGAACTCT TTCGATATTA     1500

ATAATATCTA AACTCGTGTA GCAGTCATTT CCATTTTTTT TGATCCAGTA AATA           1554
```

(2) INFORMATION FOR SEQ ID NO: 4:

(i) SEQUENCE CHARACTERISTICS:
        (A) LENGTH: 4344 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION:668..4141

(ix) FEATURE:
        (A) NAME/KEY: misc_feature
        (B) LOCATION:1..4344
        (D) OTHER INFORMATION:/note= "encompasses entire sequence
            of SEQ ID NO (SID) 2: from nt position 474 to 2034 in SID
            4"

(ix) FEATURE:
        (A) NAME/KEY: misc_feature
        (B) LOCATION:1..4344
        (D) OTHER INFORMATION:/note= "also encompasses part of
            the sequence of SID 3: from nt position 2994 to 4344 in
            SID 4"

(ix) FEATURE:
        (A) NAME/KEY: misc_feature
        (B) LOCATION:1..4344
        (D) OTHER INFORMATION:/note= "SID 3 shows additional
            nucleotides, located 3' from the sequence shown in SID 4
            (1352-1554 in SID 4)"

(xi) SEQUENCE DESCRIPTION: SEQ ID NO: 4:

```
GAATTCGAGC TCGGTACCTT TTCAGTGTAT CGTTTCCCTT CCATCAGGTT TTCAAATTGA       60

AAAGCCGAAT GATTTGAAAC TTGTTTACGA TGTAAGTCAT TTGTCTATGA CGAAAGATAC     120

GTGTAAAAAA CGTATTGAGA TTGATGAATG TGGACAAGTA GAAATTGACT TACAAGTATT     180

AAAGATTAAG GGTGTCCTTT CTTTTATCGG AAATTTCTCT ATTGAACCTA TTCTGTGTGA     240

AAACATGTAT ACAACGGTTG ATAGAGATCC GTCTATTTCC TTAAGTTTCC AAGATACGGT     300

ATATGTGGAC CATATTTTAA AATATAGCGT CCAACAACTA CCATATTATG TAATTGATGG     360

TGATCATATT CAAGTACGTG ATTTACAAAT CAAACTGATG AAAGAGAATC CGCAATCTGC     420

TCAAGTATCA GGTTTGTTTT GTTTTGTATA TGAGTAAGAA CCGAAGGTTT GTAAAAAGA     480

AATAGGAATA AATACTATCC ATTTTTTCAA GAAATATTTT TTTATTAGAA AGGAATCTTT     540

CTTACACGGG AAAATCCTAA GATTGAGAGT AAAGATATAT ATATATAAAT ACAATAAAGA     600

GTTTGTCAGG ATTTTTGAAA GATATGATAT GAACATGCAC TAGATTTATA GTATAGGAGG     660
```

```
AAAAAGT ATG AAT CGA AAT AAT CAA AAT GAA TAT GAA ATT ATT GAT GCC        709
        Met Asn Arg Asn Asn Gln Asn Glu Tyr Glu Ile Ile Asp Ala
        1               5                   10

CCC CAT TGT GGG TGT CCA TCA GAT GAC GAT GTG AGG TAT CCT TTG GCA        757
Pro His Cys Gly Cys Pro Ser Asp Asp Asp Val Arg Tyr Pro Leu Ala
15                  20                  25                  30

AGT GAC CCA AAT GCA GCG TTA CAA AAT ATG AAC TAT AAA GAT TAC TTA        805
Ser Asp Pro Asn Ala Ala Leu Gln Asn Met Asn Tyr Lys Asp Tyr Leu
                35                  40                  45

CAA ATG ACA GAT GAG GAC TAC ACT GAT TCT TAT ATA AAT CCT AGT TTA        853
Gln Met Thr Asp Glu Asp Tyr Thr Asp Ser Tyr Ile Asn Pro Ser Leu
            50                  55                  60

TCT ATT AGT GGT AGA GAT GCA GTT CAG ACT GCG CTT ACT GTT GTT GGG        901
Ser Ile Ser Gly Arg Asp Ala Val Gln Thr Ala Leu Thr Val Val Gly
        65                  70                  75

AGA ATA CTC GGG GCT TTA GGT GTT CCG TTT TCT GGA CAA ATA GTG AGT        949
Arg Ile Leu Gly Ala Leu Gly Val Pro Phe Ser Gly Gln Ile Val Ser
    80                  85                  90

TTT TAT CAA TTC CTT TTA AAT ACA CTG TGG CCA GTT AAT GAT ACA GCT        997
Phe Tyr Gln Phe Leu Leu Asn Thr Leu Trp Pro Val Asn Asp Thr Ala
95                  100                 105                 110

ATA TGG GAA GCT TTC ATG CGA CAG GTG GAG GAA CTT GTC AAT CAA CAA       1045
Ile Trp Glu Ala Phe Met Arg Gln Val Glu Glu Leu Val Asn Gln Gln
                115                 120                 125

ATA ACA GAA TTT GCA AGA AAT CAG GCA CTT GCA AGA TTG CAA GGA TTA       1093
Ile Thr Glu Phe Ala Arg Asn Gln Ala Leu Ala Arg Leu Gln Gly Leu
            130                 135                 140

GGA GAC TCT TTT AAT GTA TAT CAA CGT TCC CTT CAA AAT TGG TTG GCT       1141
Gly Asp Ser Phe Asn Val Tyr Gln Arg Ser Leu Gln Asn Trp Leu Ala
        145                 150                 155

GAT CGA AAT GAT ACA CGA AAT TTA AGT GTT GTT CGT GCT CAA TTT ATA       1189
Asp Arg Asn Asp Thr Arg Asn Leu Ser Val Val Arg Ala Gln Phe Ile
    160                 165                 170

GCT TTA GAC CTT GAT TTT GTT AAT GCT ATT CCA TTG TTT GCA GTA AAT       1237
Ala Leu Asp Leu Asp Phe Val Asn Ala Ile Pro Leu Phe Ala Val Asn
175                 180                 185                 190

GGA CAG CAG GTT CCA TTA CTG TCA GTA TAT GCA CAA GCT GTG AAT TTA       1285
Gly Gln Gln Val Pro Leu Leu Ser Val Tyr Ala Gln Ala Val Asn Leu
                195                 200                 205

CAT TTG TTA TTA TTA AAA GAT GCA TCT CTT TTT GGA GAA GGA TGG GGA       1333
His Leu Leu Leu Leu Lys Asp Ala Ser Leu Phe Gly Glu Gly Trp Gly
            210                 215                 220

TTC ACA CAG GGG GAA ATT TCC ACA TAT TAT GAC CGT CAA TTG GAA CTA       1381
Phe Thr Gln Gly Glu Ile Ser Thr Tyr Tyr Asp Arg Gln Leu Glu Leu
        225                 230                 235

ACC GCT AAG TAC ACT AAT TAC TGT GAA ACT TGG TAT AAT ACA GGT TTA       1429
Thr Ala Lys Tyr Thr Asn Tyr Cys Glu Thr Trp Tyr Asn Thr Gly Leu
    240                 245                 250

GAT CGT TTA AGA GGA ACA AAT ACT GAA AGT TGG TTA AGA TAT CAT CAA       1477
Asp Arg Leu Arg Gly Thr Asn Thr Glu Ser Trp Leu Arg Tyr His Gln
255                 260                 265                 270

TTC CGT AGA GAA ATG ACT TTA GTG GTA TTA GAT GTT GTG GCG CTA TTT       1525
Phe Arg Arg Glu Met Thr Leu Val Val Leu Asp Val Val Ala Leu Phe
                275                 280                 285

CCA TAT TAT GAT GTA CGA CTT TAT CCA ACG GGA TCA AAC CCA CAG CTT       1573
Pro Tyr Tyr Asp Val Arg Leu Tyr Pro Thr Gly Ser Asn Pro Gln Leu
            290                 295                 300

ACA CGT GAG GTA TAT ACA GAT CCG ATT GTA TTT AAT CCA CCA GCT AAT       1621
Thr Arg Glu Val Tyr Thr Asp Pro Ile Val Phe Asn Pro Pro Ala Asn
```

-continued

|  |  |  |  |  |  |  |  |  |  |  |  |  |  |  |  |
|---|---|---|---|---|---|---|---|---|---|---|---|---|---|---|---|
|  |  | 305 |  |  |  | 310 |  |  |  |  | 315 |  |  |  |  |
| GTT | GGA | CTT | TGC | CGA | CGT | TGG | GGT | ACT | AAT | CCC | TAT | AAT | ACT | TTT | TCT | 1669 |
| Val | Gly | Leu | Cys | Arg | Arg | Trp | Gly | Thr | Asn | Pro | Tyr | Asn | Thr | Phe | Ser |
|  |  | 320 |  |  |  | 325 |  |  |  |  | 330 |  |  |  |  |
| GAG | CTC | GAA | AAT | GCC | TTC | ATT | CGC | CCA | CCA | CAT | CTT | TTT | GAT | AGG | CTG | 1717 |
| Glu | Leu | Glu | Asn | Ala | Phe | Ile | Arg | Pro | Pro | His | Leu | Phe | Asp | Arg | Leu |
| 335 |  |  |  |  | 340 |  |  |  |  | 345 |  |  |  |  | 350 |
| AAT | AGC | TTA | ACA | ATC | AGC | AGT | AAT | CGA | TTT | CCA | GTT | TCA | TCT | AAT | TTT | 1765 |
| Asn | Ser | Leu | Thr | Ile | Ser | Ser | Asn | Arg | Phe | Pro | Val | Ser | Ser | Asn | Phe |
|  |  |  |  | 355 |  |  |  |  | 360 |  |  |  |  | 365 |  |
| ATG | GAT | TAT | TGG | TCA | GGA | CAT | ACG | TTA | CGC | CGT | AGT | TAT | CTG | AAC | GAT | 1813 |
| Met | Asp | Tyr | Trp | Ser | Gly | His | Thr | Leu | Arg | Arg | Ser | Tyr | Leu | Asn | Asp |
|  |  |  | 370 |  |  |  |  | 375 |  |  |  |  | 380 |  |  |
| TCA | GCA | GTA | CAA | GAA | GAT | AGT | TAT | GGC | CTA | ATT | ACA | ACC | ACA | AGA | GCA | 1861 |
| Ser | Ala | Val | Gln | Glu | Asp | Ser | Tyr | Gly | Leu | Ile | Thr | Thr | Thr | Arg | Ala |
| 385 |  |  |  |  |  | 390 |  |  |  |  | 395 |  |  |  |  |
| ACA | ATT | AAT | CCC | GGA | GTT | GAT | GGA | ACA | AAC | CGC | ATA | GAG | TCA | ACG | GCA | 1909 |
| Thr | Ile | Asn | Pro | Gly | Val | Asp | Gly | Thr | Asn | Arg | Ile | Glu | Ser | Thr | Ala |
|  | 400 |  |  |  |  | 405 |  |  |  |  | 410 |  |  |  |  |
| GTA | GAT | TTT | CGT | TCT | GCA | TTG | ATA | GGT | ATA | TAT | GGC | GTG | AAT | AGA | GCT | 1957 |
| Val | Asp | Phe | Arg | Ser | Ala | Leu | Ile | Gly | Ile | Tyr | Gly | Val | Asn | Arg | Ala |
| 415 |  |  |  |  | 420 |  |  |  |  | 425 |  |  |  |  | 430 |
| TCT | TTT | GTC | CCA | GGA | GGC | TTG | TTT | AAT | GGT | ACG | ACT | TCT | CCT | GCT | AAT | 2005 |
| Ser | Phe | Val | Pro | Gly | Gly | Leu | Phe | Asn | Gly | Thr | Thr | Ser | Pro | Ala | Asn |
|  |  |  |  | 435 |  |  |  |  | 440 |  |  |  |  | 445 |  |
| GGA | GGA | TGT | AGA | GAT | CTC | TAT | GAT | ACA | AAT | GAT | GAA | TTA | CCA | CCA | GAT | 2053 |
| Gly | Gly | Cys | Arg | Asp | Leu | Tyr | Asp | Thr | Asn | Asp | Glu | Leu | Pro | Pro | Asp |
|  |  |  | 450 |  |  |  |  | 455 |  |  |  |  | 460 |  |  |
| GAA | AGT | ACC | GGA | AGT | TCA | ACC | CAT | AGA | CTA | TCT | CAT | GTT | ACC | TTT | TTT | 2101 |
| Glu | Ser | Thr | Gly | Ser | Ser | Thr | His | Arg | Leu | Ser | His | Val | Thr | Phe | Phe |
|  |  | 465 |  |  |  |  | 470 |  |  |  |  | 475 |  |  |  |
| AGC | TTT | CAA | ACT | AAT | CAG | GCT | GGA | TCT | ATA | GCT | AAT | GCA | GGA | AGT | GTA | 2149 |
| Ser | Phe | Gln | Thr | Asn | Gln | Ala | Gly | Ser | Ile | Ala | Asn | Ala | Gly | Ser | Val |
|  | 480 |  |  |  |  | 485 |  |  |  |  | 490 |  |  |  |  |
| CCT | ACT | TAT | GTT | TGG | ACC | CGT | CGT | GAT | GTG | GAC | CTT | AAT | AAT | ACG | ATT | 2197 |
| Pro | Thr | Tyr | Val | Trp | Thr | Arg | Arg | Asp | Val | Asp | Leu | Asn | Asn | Thr | Ile |
| 495 |  |  |  |  | 500 |  |  |  |  | 505 |  |  |  |  | 510 |
| ACC | CCA | AAT | AGA | ATT | ACA | CAA | TTA | CCA | TTG | GTA | AAG | GCA | TCT | GCA | CCT | 2245 |
| Thr | Pro | Asn | Arg | Ile | Thr | Gln | Leu | Pro | Leu | Val | Lys | Ala | Ser | Ala | Pro |
|  |  |  |  | 515 |  |  |  |  | 520 |  |  |  |  | 525 |  |
| GTT | TCG | GGT | ACT | ACG | GTC | TTA | AAA | GGT | CCA | GGA | TTT | ACA | GGA | GGG | GGT | 2293 |
| Val | Ser | Gly | Thr | Thr | Val | Leu | Lys | Gly | Pro | Gly | Phe | Thr | Gly | Gly | Gly |
|  |  |  | 530 |  |  |  |  | 535 |  |  |  |  | 540 |  |  |
| ATA | CTC | CGA | AGA | ACA | ACT | AAT | GGC | ACA | TTT | GGA | ACG | TTA | AGA | GTA | ACG | 2341 |
| Ile | Leu | Arg | Arg | Thr | Thr | Asn | Gly | Thr | Phe | Gly | Thr | Leu | Arg | Val | Thr |
|  |  | 545 |  |  |  |  | 550 |  |  |  |  | 555 |  |  |  |
| GTT | AAT | TCA | CCA | TTA | ACA | CAA | CAA | TAT | CGC | CTA | AGA | GTT | CGT | TTT | GCC | 2389 |
| Val | Asn | Ser | Pro | Leu | Thr | Gln | Gln | Tyr | Arg | Leu | Arg | Val | Arg | Phe | Ala |
|  | 560 |  |  |  |  | 565 |  |  |  |  | 570 |  |  |  |  |
| TCA | ACA | GGA | AAT | TTC | AGT | ATA | AGG | GTA | CTC | CGT | GGA | GGG | GTT | TCT | ATC | 2437 |
| Ser | Thr | Gly | Asn | Phe | Ser | Ile | Arg | Val | Leu | Arg | Gly | Gly | Val | Ser | Ile |
| 575 |  |  |  |  | 580 |  |  |  |  | 585 |  |  |  |  | 590 |
| GGT | GAT | GTT | AGA | TTA | GGG | AGC | ACA | ATG | AAC | AGA | GGG | CAG | GAA | CTA | ACT | 2485 |
| Gly | Asp | Val | Arg | Leu | Gly | Ser | Thr | Met | Asn | Arg | Gly | Gln | Glu | Leu | Thr |
|  |  |  | 595 |  |  |  |  | 600 |  |  |  |  | 605 |  |  |
| TAC | GAA | TCC | TTT | TTC | ACA | AGA | GAG | TTT | ACT | ACT | ACT | GGT | CCG | TTC | AAT | 2533 |
| Tyr | Glu | Ser | Phe | Phe | Thr | Arg | Glu | Phe | Thr | Thr | Thr | Gly | Pro | Phe | Asn |
|  |  | 610 |  |  |  |  | 615 |  |  |  |  | 620 |  |  |  |
| CCG | CCT | TTT | ACA | TTT | ACA | CAA | GCT | CAA | GAG | ATT | CTA | ACA | GTG | AAT | GCA | 2581 |

```
Pro Pro Phe Thr Phe Thr Gln Ala Gln Glu Ile Leu Thr Val Asn Ala
        625                 630                 635

GAA GGT GTT AGC ACC GGT GGT GAA TAT TAT ATA GAT AGA ATT GAA ATT   2629
Glu Gly Val Ser Thr Gly Gly Glu Tyr Tyr Ile Asp Arg Ile Glu Ile
640                 645                 650

GTC CCT GTG AAT CCG GCA CGA GAA GCG GAA GAG GAT TTA GAA GCG GCG   2677
Val Pro Val Asn Pro Ala Arg Glu Ala Glu Glu Asp Leu Glu Ala Ala
655                 660                 665                 670

AAG AAA GCG GTG GCG AGC TTG TTT ACA CGT ACA AGG GAC GGA TTA CAG   2725
Lys Lys Ala Val Ala Ser Leu Phe Thr Arg Thr Arg Asp Gly Leu Gln
                675                 680                 685

GTA AAT GTG ACA GAT TAT CAA GTG GAC CAA GCG GCA AAT TTA GTG TCA   2773
Val Asn Val Thr Asp Tyr Gln Val Asp Gln Ala Ala Asn Leu Val Ser
            690                 695                 700

TGC TTA TCC GAT GAA CAA TAT GGG CAT GAC AAA AAG ATG TTA TTG GAA   2821
Cys Leu Ser Asp Glu Gln Tyr Gly His Asp Lys Lys Met Leu Leu Glu
        705                 710                 715

GCG GTA AGA GCG GCA AAA CGC CTC AGC CGC GAA CGC AAC TTA CTT CAA   2869
Ala Val Arg Ala Ala Lys Arg Leu Ser Arg Glu Arg Asn Leu Leu Gln
    720                 725                 730

GAT CCA GAT TTT AAT ACA ATC AAT AGT ACA GAA GAG AAT GGC TGG AAG   2917
Asp Pro Asp Phe Asn Thr Ile Asn Ser Thr Glu Glu Asn Gly Trp Lys
735                 740                 745                 750

GCA AGT AAC GGT GTT ACT ATT AGC GAG GGC GGT CCA TTC TTT AAA GGT   2965
Ala Ser Asn Gly Val Thr Ile Ser Glu Gly Gly Pro Phe Phe Lys Gly
                755                 760                 765

CGT GCA CTT CAG TTA GCA AGC GCA AGA GAA AAT TAT CCA ACA TAC ATT   3013
Arg Ala Leu Gln Leu Ala Ser Ala Arg Glu Asn Tyr Pro Thr Tyr Ile
            770                 775                 780

TAT CAA AAA GTA GAT GCA TCG GTG TTA AAG CCT TAT ACA CGC TAT AGA   3061
Tyr Gln Lys Val Asp Ala Ser Val Leu Lys Pro Tyr Thr Arg Tyr Arg
        785                 790                 795

CTA GAT GGA TTT GTG AAG AGT AGT CAA GAT TTA GAA ATT GAT CTC ATC   3109
Leu Asp Gly Phe Val Lys Ser Ser Gln Asp Leu Glu Ile Asp Leu Ile
    800                 805                 810

CAC CAT CAT AAA GTC CAT CTT GTA AAA AAT GTA CCA GAT AAT TTA GTA   3157
His His His Lys Val His Leu Val Lys Asn Val Pro Asp Asn Leu Val
815                 820                 825                 830

TCT GAT ACT TAC TCA GAT GGT TCT TGC AGC GGA ATC AAC CGT TGT GAT   3205
Ser Asp Thr Tyr Ser Asp Gly Ser Cys Ser Gly Ile Asn Arg Cys Asp
                835                 840                 845

GAA CAG CAT CAG GTA GAT ATG CAG CTA GAT GCG GAG CAT CAT CCA ATG   3253
Glu Gln His Gln Val Asp Met Gln Leu Asp Ala Glu His His Pro Met
            850                 855                 860

GAT TGC TGT GAA GCG GCT CAA ACA CAT GAG TTT TCT TCC TAT ATT AAT   3301
Asp Cys Cys Glu Ala Ala Gln Thr His Glu Phe Ser Ser Tyr Ile Asn
        865                 870                 875

ACA GGG GAT CTA AAT GCA AGT GTA GAT CAG GGC ATT TGG GTT GTA TTA   3349
Thr Gly Asp Leu Asn Ala Ser Val Asp Gln Gly Ile Trp Val Val Leu
    880                 885                 890

AAA GTT CGA ACA ACA GAT GGG TAT GCG ACG TTA GGA AAT CTT GAA TTG   3397
Lys Val Arg Thr Thr Asp Gly Tyr Ala Thr Leu Gly Asn Leu Glu Leu
895                 900                 905                 910

GTA GAG GTT GGG CCA TTA TCG GGT GAA TCT CTA GAA CGG GAA CAA AGA   3445
Val Glu Val Gly Pro Leu Ser Gly Glu Ser Leu Glu Arg Glu Gln Arg
                915                 920                 925

GAT AAT GCG AAA TGG AAT GCA GAG CTA GGA AGA AAA CGT GCA GAA ATA   3493
Asp Asn Ala Lys Trp Asn Ala Glu Leu Gly Arg Lys Arg Ala Glu Ile
            930                 935                 940
```

```
GAT CGT GTG TAT TTA GCT GCG AAA CAA GCA ATT AAT CAT CTG TTT GTA          3541
Asp Arg Val Tyr Leu Ala Ala Lys Gln Ala Ile Asn His Leu Phe Val
            945                 950                 955

GAC TAT CAA GAT CAA CAA TTA AAT CCA GAA ATT GGG CTA GCA GAA ATT          3589
Asp Tyr Gln Asp Gln Gln Leu Asn Pro Glu Ile Gly Leu Ala Glu Ile
960                 965                 970

AAT GAA GCT TCA AAT CTT GTA GAG TCA ATT TCG GGT GTA TAT AGT GAT          3637
Asn Glu Ala Ser Asn Leu Val Glu Ser Ile Ser Gly Val Tyr Ser Asp
975                 980                 985                 990

ACA CTA TTA CAG ATT CCT GGG ATT AAC TAC GAA ATT TAC ACA GAG TTA          3685
Thr Leu Leu Gln Ile Pro Gly Ile Asn Tyr Glu Ile Tyr Thr Glu Leu
            995                 1000                1005

TCC GAT CGC TTA CAA CAA GCA TCG TAT CTG TAT ACG TCT AGA AAT GCG          3733
Ser Asp Arg Leu Gln Gln Ala Ser Tyr Leu Tyr Thr Ser Arg Asn Ala
            1010                1015                1020

GTG CAA AAT GGA GAC TTT AAC AGT GGT CTA GAT AGT TGG AAT ACA ACT          3781
Val Gln Asn Gly Asp Phe Asn Ser Gly Leu Asp Ser Trp Asn Thr Thr
            1025                1030                1035

ATG GAT GCA TCG GTT CAG CAA GAT GGC AAT ATG CAT TTC TTA GTT CTT          3829
Met Asp Ala Ser Val Gln Gln Asp Gly Asn Met His Phe Leu Val Leu
            1040                1045                1050

TCG CAT TGG GAT GCA CAA GTT TCC CAA CAA TTG AGA GTA AAT CCG AAT          3877
Ser His Trp Asp Ala Gln Val Ser Gln Gln Leu Arg Val Asn Pro Asn
1055                1060                1065                1070

TGT AAG TAT GTC TTA CGT GTG ACA GCA AGA AAA GTA GGA GGC GGA GAT          3925
Cys Lys Tyr Val Leu Arg Val Thr Ala Arg Lys Val Gly Gly Gly Asp
            1075                1080                1085

GGA TAC GTC ACA ATC CGA GAT GGC GCT CAT CAC CAA GAA ACT CTT ACA          3973
Gly Tyr Val Thr Ile Arg Asp Gly Ala His His Gln Glu Thr Leu Thr
            1090                1095                1100

TTT AAT GCA TGT GAC TAC GAT GTA AAT GGT ACG TAT GTC AAT GAC AAT          4021
Phe Asn Ala Cys Asp Tyr Asp Val Asn Gly Thr Tyr Val Asn Asp Asn
            1105                1110                1115

TCG TAT ATA ACA GAA GAA GTG GTA TTC TAC CCA GAG ACA AAA CAT ATG          4069
Ser Tyr Ile Thr Glu Glu Val Val Phe Tyr Pro Glu Thr Lys His Met
            1120                1125                1130

TGG GTA GAG GTG AGT GAA TCC GAA GGT TCA TTC TAT ATA GAC AGT ATT          4117
Trp Val Glu Val Ser Glu Ser Glu Gly Ser Phe Tyr Ile Asp Ser Ile
1135                1140                1145                1150

GAG TTT ATT GAA ACA CAA GAG TAG AAGAGGGGGA TCCTAACGTA TAGCAACTAT         4171
Glu Phe Ile Glu Thr Gln Glu  *
                1155

GAGAGGATAC TCCGTACAAA CAAAGATTAA AAAAAGGTAA AATGAATAGA ACCCCCTACT        4231

GGTAGAAGGA CCGATAGGGG GTTCTTACAT GAAAAAATGT AGCTGTTTAC TAAGGTGTAT        4291

AAAAAACAGC ATATCTGATA GAAAAAAGTG AGTACCTTAT AAAGAAAGAA TTC              4344

(2) INFORMATION FOR SEQ ID NO: 5:

(i) SEQUENCE CHARACTERISTICS:
         (A) LENGTH: 1157 amino acids
         (B) TYPE: amino acid
         (D) TOPOLOGY: linear (ii) MOLECULE TYPE: protein (xi) SEQUENCE DESCRIPTION: SEQ ID NO: 5:

Met Asn Arg Asn Asn Gln Asn Glu Tyr Glu Ile Ile Asp Ala Pro His
 1               5                  10                  15

Cys Gly Cys Pro Ser Asp Asp Asp Val Arg Tyr Pro Leu Ala Ser Asp
            20                  25                  30
```

-continued

```
Pro Asn Ala Ala Leu Gln Asn Met Asn Tyr Lys Asp Tyr Leu Gln Met
         35                  40                  45
Thr Asp Glu Asp Tyr Thr Asp Ser Tyr Ile Asn Pro Ser Leu Ser Ile
 50                  55                  60
Ser Gly Arg Asp Ala Val Gln Thr Ala Leu Thr Val Gly Arg Ile
 65                  70                  75                  80
Leu Gly Ala Leu Gly Val Pro Phe Ser Gly Gln Ile Val Ser Phe Tyr
                 85                  90                  95
Gln Phe Leu Leu Asn Thr Leu Trp Pro Val Asn Asp Thr Ala Ile Trp
             100                 105                 110
Glu Ala Phe Met Arg Gln Val Glu Glu Leu Val Asn Gln Gln Ile Thr
             115                 120                 125
Glu Phe Ala Arg Asn Gln Ala Leu Ala Arg Leu Gln Gly Leu Gly Asp
         130                 135                 140
Ser Phe Asn Val Tyr Gln Arg Ser Leu Gln Asn Trp Leu Ala Asp Arg
145                 150                 155                 160
Asn Asp Thr Arg Asn Leu Ser Val Val Arg Ala Gln Phe Ile Ala Leu
                 165                 170                 175
Asp Leu Asp Phe Val Asn Ala Ile Pro Leu Phe Ala Val Asn Gly Gln
             180                 185                 190
Gln Val Pro Leu Leu Ser Val Tyr Ala Gln Ala Val Asn Leu His Leu
         195                 200                 205
Leu Leu Leu Lys Asp Ala Ser Leu Phe Gly Glu Gly Trp Gly Phe Thr
     210                 215                 220
Gln Gly Glu Ile Ser Thr Tyr Tyr Asp Arg Gln Leu Glu Leu Thr Ala
225                 230                 235                 240
Lys Tyr Thr Asn Tyr Cys Glu Thr Trp Tyr Asn Thr Gly Leu Asp Arg
                 245                 250                 255
Leu Arg Gly Thr Asn Thr Glu Ser Trp Leu Arg Tyr His Gln Phe Arg
             260                 265                 270
Arg Glu Met Thr Leu Val Val Leu Asp Val Val Ala Leu Phe Pro Tyr
         275                 280                 285
Tyr Asp Val Arg Leu Tyr Pro Thr Gly Ser Asn Pro Gln Leu Thr Arg
     290                 295                 300
Glu Val Tyr Thr Asp Pro Ile Val Phe Asn Pro Pro Ala Asn Val Gly
305                 310                 315                 320
Leu Cys Arg Arg Trp Gly Thr Asn Pro Tyr Asn Thr Phe Ser Glu Leu
                 325                 330                 335
Glu Asn Ala Phe Ile Arg Pro Pro His Leu Phe Asp Arg Leu Asn Ser
             340                 345                 350
Leu Thr Ile Ser Ser Asn Arg Phe Pro Val Ser Ser Asn Phe Met Asp
         355                 360                 365
Tyr Trp Ser Gly His Thr Leu Arg Arg Ser Tyr Leu Asn Asp Ser Ala
     370                 375                 380
Val Gln Glu Asp Ser Tyr Gly Leu Ile Thr Thr Thr Arg Ala Thr Ile
385                 390                 395                 400
Asn Pro Gly Val Asp Gly Thr Asn Arg Ile Glu Ser Thr Ala Val Asp
                 405                 410                 415
Phe Arg Ser Ala Leu Ile Gly Ile Tyr Gly Val Asn Arg Ala Ser Phe
             420                 425                 430
Val Pro Gly Gly Leu Phe Asn Gly Thr Thr Ser Pro Ala Asn Gly Gly
         435                 440                 445
```

-continued

```
Cys Arg Asp Leu Tyr Asp Thr Asn Asp Glu Leu Pro Pro Asp Glu Ser
    450                 455                 460
Thr Gly Ser Ser Thr His Arg Leu Ser His Val Thr Phe Phe Ser Phe
465                 470                 475                 480
Gln Thr Asn Gln Ala Gly Ser Ile Ala Asn Ala Gly Ser Val Pro Thr
                    485                 490                 495
Tyr Val Trp Thr Arg Arg Asp Val Asp Leu Asn Asn Thr Ile Thr Pro
                500                 505                 510
Asn Arg Ile Thr Gln Leu Pro Leu Val Lys Ala Ser Ala Pro Val Ser
            515                 520                 525
Gly Thr Thr Val Leu Lys Gly Pro Gly Phe Thr Gly Gly Ile Leu
        530                 535                 540
Arg Arg Thr Thr Asn Gly Thr Phe Gly Thr Leu Arg Val Thr Val Asn
545                 550                 555                 560
Ser Pro Leu Thr Gln Gln Tyr Arg Leu Arg Val Arg Phe Ala Ser Thr
                565                 570                 575
Gly Asn Phe Ser Ile Arg Val Leu Arg Gly Gly Val Ser Ile Gly Asp
                580                 585                 590
Val Arg Leu Gly Ser Thr Met Asn Arg Gly Gln Glu Leu Thr Tyr Glu
                595                 600                 605
Ser Phe Phe Thr Arg Glu Phe Thr Thr Thr Gly Pro Phe Asn Pro Pro
        610                 615                 620
Phe Thr Phe Thr Gln Ala Gln Glu Ile Leu Thr Val Asn Ala Glu Gly
625                 630                 635                 640
Val Ser Thr Gly Gly Glu Tyr Tyr Ile Asp Arg Ile Glu Ile Val Pro
                645                 650                 655
Val Asn Pro Ala Arg Glu Ala Glu Glu Asp Leu Glu Ala Ala Lys Lys
                660                 665                 670
Ala Val Ala Ser Leu Phe Thr Arg Thr Arg Asp Gly Leu Gln Val Asn
            675                 680                 685
Val Thr Asp Tyr Gln Val Asp Gln Ala Ala Asn Leu Val Ser Cys Leu
690                 695                 700
Ser Asp Glu Gln Tyr Gly His Asp Lys Lys Met Leu Leu Glu Ala Val
705                 710                 715                 720
Arg Ala Ala Lys Arg Leu Ser Arg Glu Arg Asn Leu Leu Gln Asp Pro
                725                 730                 735
Asp Phe Asn Thr Ile Asn Ser Thr Glu Glu Asn Gly Trp Lys Ala Ser
                740                 745                 750
Asn Gly Val Thr Ile Ser Glu Gly Gly Pro Phe Phe Lys Gly Arg Ala
            755                 760                 765
Leu Gln Leu Ala Ser Ala Arg Glu Asn Tyr Pro Thr Tyr Ile Tyr Gln
        770                 775                 780
Lys Val Asp Ala Ser Val Leu Lys Pro Tyr Thr Arg Tyr Arg Leu Asp
785                 790                 795                 800
Gly Phe Val Lys Ser Ser Gln Asp Leu Glu Ile Asp Leu Ile His His
                805                 810                 815
His Lys Val His Leu Val Lys Asn Val Pro Asp Asn Leu Val Ser Asp
                820                 825                 830
Thr Tyr Ser Asp Gly Ser Cys Ser Gly Ile Asn Arg Cys Asp Glu Gln
            835                 840                 845
His Gln Val Asp Met Gln Leu Asp Ala Glu His Pro Met Asp Cys
        850                 855                 860
Cys Glu Ala Ala Gln Thr His Glu Phe Ser Ser Tyr Ile Asn Thr Gly
```

-continued

```
865                 870                 875                 880

Asp Leu Asn Ala Ser Val Asp Gln Gly Ile Trp Val Val Leu Lys Val
                885                 890                 895

Arg Thr Thr Asp Gly Tyr Ala Thr Leu Gly Asn Leu Glu Leu Val Glu
                900                 905                 910

Val Gly Pro Leu Ser Gly Glu Ser Leu Glu Arg Glu Gln Arg Asp Asn
            915                 920                 925

Ala Lys Trp Asn Ala Glu Leu Gly Arg Lys Arg Ala Glu Ile Asp Arg
        930                 935                 940

Val Tyr Leu Ala Ala Lys Gln Ala Ile Asn His Leu Phe Val Asp Tyr
945                 950                 955                 960

Gln Asp Gln Gln Leu Asn Pro Glu Ile Gly Leu Ala Glu Ile Asn Glu
                965                 970                 975

Ala Ser Asn Leu Val Glu Ser Ile Ser Gly Val Tyr Ser Asp Thr Leu
            980                 985                 990

Leu Gln Ile Pro Gly Ile Asn Tyr Glu Ile Tyr Thr Glu Leu Ser Asp
            995                 1000                1005

Arg Leu Gln Gln Ala Ser Tyr Leu Tyr Thr Ser Arg Asn Ala Val Gln
        1010                1015                1020

Asn Gly Asp Phe Asn Ser Gly Leu Asp Ser Trp Asn Thr Thr Met Asp
1025                1030                1035                1040

Ala Ser Val Gln Gln Asp Gly Asn Met His Phe Leu Val Leu Ser His
                1045                1050                1055

Trp Asp Ala Gln Val Ser Gln Gln Leu Arg Val Asn Pro Asn Cys Lys
                1060                1065                1070

Tyr Val Leu Arg Val Thr Ala Arg Lys Val Gly Gly Gly Asp Gly Tyr
            1075                1080                1085

Val Thr Ile Arg Asp Gly Ala His His Gln Glu Thr Leu Thr Phe Asn
            1090                1095                1100

Ala Cys Asp Tyr Asp Val Asn Gly Thr Tyr Val Asn Asp Asn Ser Tyr
1105                1110                1115                1120

Ile Thr Glu Glu Val Val Phe Tyr Pro Glu Thr Lys His Met Trp Val
                1125                1130                1135

Glu Val Ser Glu Ser Glu Gly Ser Phe Tyr Ile Asp Ser Ile Glu Phe
            1140                1145                1150

Ile Glu Thr Gln Glu
        1155
```

We claim:

1. A transformed plant cell, comprising in its genome, a DNA sequence encoding the protein of SEQ ID No. 5 or an insecticidally effective part thereof.

2. A transformed plant cell, comprising in its genome, a chimeric gene comprising a DNA sequence encoding the protein with the amino acid sequence of position 44 to position 658 in SEQ ID No. 5.

3. A plant genome comprising, integrated therein, a chimeric gene comprising a DNA sequence encoding the protein of SEQ ID No. 5 or an insecticidally effective part thereof.

4. A plant tissue, the cells of which have the plant genome of claim 3.

5. A process for rendering a plant resistant to insects, comprising the step of: transforming a plant cell with the DNA sequence of claim 1 or 2 and regenerating a plant from said transformed cell.

6. A process for producing insect-resistant plants or reproduction material of said plants, comprising the following steps: a) stably integrating a chimeric gene comprising a DNA sequence encoding the protein of SEQ ID No. 5 or an insecticidally effective portion thereof in the genome of plant cells; b) regenerating stably transformed plants or reproduction material thereof from said transformed plant cells; and c) biologically replicating said regenerated plants or reproduction material.

7. A process for controlling an insect pest, selected from the following group: *Agrotis ipsilon, Spodoptera exigua, Spodoptera littoralis, Spodoptera frugiperda, Mamestra brassica, Heliothis virescens, Ostrinia nubilalis* and *Plutella xylostella*; said process comprising the step of contacting the pest with the BTS02618A protoxin of SEQ ID No. 5 or an insecticidally effective portion thereof, wherein said protein or its insecticidally effective portion is produced in a plant cell.

8. A process for protecting plants against Noctuidae, Pyralidae and Yponomeutidae, comprising the steps of: transforming the genome of a plant with the DNA sequence of claim 1 and obtaining reproduction material from said plant.

9. A process for controlling or killing *Ostrinia nubilalis, Spodoptera frugiperda* and *Agrotis ipsilon* on corn plants, comprising the steps of: a) stably integrating a chimeric gene, comprising a DNA sequence encoding the BTS02618A protein of SEQ ID No. 5 or an insecticidally effective portion thereof, in corn cells; b) regenerating transformed corn plants or reproduction material thereof comprising said chimeric gene from said transformed corn cells; c) biologically replicating said regenerated plants or reproduction material thereof; and d) planting said corn plants or reproduction material thereof comprising said chimeric gene in a field.

10. A plant cell, comprising a DNA with the nucleotide sequence of SEQ ID No. 4 from nucleotide position 668 to nucleotide position 2641 or comprising a DNA with the nucleotide sequence of SEQ ID No. 4 from nucleotide position 797 to nucleotide position 2641.

11. A plant cell comprising a DNA selected from the following group:

a) a DNA sequence which is obtainable from the strain BTS02618A with accession Number BCCM-LMG P-12953 and which encodes a protein with insecticidal activity against *Agrotis ipsilon, Spodoptera exigua, Spodoptera littoralis, Mamestra brassica, Heliothis virescens, Ostrinia nubilalis* and *Plutella xylostella* or fragments of said DNA encoding an insecticidally active protein portion;

b) a DNA sequence encoding a crystal protein with insecticidal activity against *Agrotis ipsilon, Spodoptera exigua, Spodoptera littoralis, Mamestra brassica, Heliothis virescens, Ostrinia nubilalis* and *Plutella xylostella* which is obtainable from the strain BTS02618A with accession number BCCM-LMG P-12953 or an insecticidally effective portion of said crystal protein; and c) a DNA sequence hybridizing to the DNA with the nucleotide sequence of SEQ ID No. 4 under stringent conditions and encoding a protein with the insecticidal activity of the protein of SEQ ID No. 5.

12. A plant comprising the plant cells of any one of claims 1, 2, 10 and 11.

13. A seed of a plant, comprising the plant cells of any one of claims 1, 2, 10 and 11.

14. The plant of claim 12, which is selected from the group of: cotton, tomato, tobacco, rapeseed, alfalfa, sunflower, lettuce, potato, rice, soybean, Brassica species and sugar beet.

15. The plant of claim 12 which is a cereal plant.

16. The plant of claim 12 which is corn.

17. A process for killing insects, comprising: planting the seed of claim 15 in a field.

* * * * *

UNITED STATES PATENT AND TRADEMARK OFFICE
CERTIFICATE OF CORRECTION

PATENT NO. : 6,028,246
DATED : February 22, 2000
INVENTOR(S) : Lambert et al.

It is certified that error appears in the above-identified patent and that said Letters Patent is hereby corrected as shown below:

On the title page, item:

Please insert categories [86] and [87] as follows:

-- [86] PCT No.: PCT/EP93/01820

§ 371 Date: March 23, 1995

§ 102(e) Date: March 23, 1995   --.

-- [87] PCT Pub. No.: WO94/05771

PCT Pub. Date: March 17, 1994   --.

Signed and Sealed this

Eighth Day of May, 2001

Attest:

NICHOLAS P. GODICI

Attesting Officer

Acting Director of the United States Patent and Trademark Office